(12) United States Patent
Schmid et al.

(10) Patent No.: US 11,322,413 B2
(45) Date of Patent: May 3, 2022

(54) SAMPLE WELL FABRICATION TECHNIQUES AND STRUCTURES FOR INTEGRATED SENSOR DEVICES

(71) Applicant: Quantum-Si Incorporated, Guilford, CT (US)

(72) Inventors: Gerard Schmid, Guilford, CT (US); James Beach, Austin, TX (US)

(73) Assignee: Quantum-Si Incorporated, Guilford, CT (US)

( * ) Notice: Subject to any disclaimer, the term of this patent is extended or adjusted under 35 U.S.C. 154(b) by 15 days.

(21) Appl. No.: 16/555,902

(22) Filed: Aug. 29, 2019

(65) Prior Publication Data
US 2020/0075426 A1   Mar. 5, 2020

Related U.S. Application Data

(60) Provisional application No. 62/724,206, filed on Aug. 29, 2018.

(51) Int. Cl.
| | | |
|---|---|---|
| *B01L 3/00* | (2006.01) | |
| *B81C 1/00* | (2006.01) | |
| *H01L 21/8234* | (2006.01) | |
| *H01L 21/02* | (2006.01) | |

(Continued)

(52) U.S. Cl.
CPC ........ *H01L 21/823493* (2013.01); *B01L 3/50* (2013.01); *B01L 3/5085* (2013.01); *B81C 1/00047* (2013.01); *B81C 1/00206* (2013.01); *G01N 33/48707* (2013.01); *G01N 33/582* (2013.01); *H01L 21/0228* (2013.01); *H01L 21/02123* (2013.01); *H01L 21/02172* (2013.01); *H01L 21/02274* (2013.01); *H01L 21/823468* (2013.01)

(58) Field of Classification Search
CPC .............. B01L 3/50; B01L 21/823493; H01L 21/823493
USPC ......................................................... 422/50
See application file for complete search history.

(56) References Cited

U.S. PATENT DOCUMENTS

| | | |
|---|---|---|
| 5,961,924 A | 10/1999 | Reichert et al. |
| 6,787,308 B2 | 9/2004 | Balasubramanian et al. |
| 6,917,726 B2 | 7/2005 | Levene et al. |

(Continued)

FOREIGN PATENT DOCUMENTS

WO   WO 2011/153962 A1   12/2011

OTHER PUBLICATIONS

International Preliminary Reporton Patentability for PCT/US2019/048836, PCT, published on Mar. 2, 2021, pp. 1-8. (Year: 2021).*

(Continued)

*Primary Examiner* — Christine T Mui
(74) *Attorney, Agent, or Firm* — Wolf, Greenfield & Sacks, P.C.

(57) ABSTRACT

Methods of forming an integrated device, and in particular forming one or more sample wells in an integrated device, are described. The methods may involve forming a metal stack over a cladding layer, forming an aperture in the metal stack, forming first spacer material within the aperture, and forming a sample well by removing some of the cladding layer to extend a depth of the aperture into the cladding layer. In the resulting sample well, at least one portion of the first spacer material is in contact with at least one layer of the metal stack.

10 Claims, 16 Drawing Sheets

(51) Int. Cl.
*G01N 33/487* (2006.01)
*G01N 33/58* (2006.01)

(56) References Cited

U.S. PATENT DOCUMENTS

| | | |
|---|---|---|
| 7,175,811 B2 | 2/2007 | Bach et al. |
| 7,426,322 B2 | 9/2008 | Hyde |
| 7,738,086 B2 | 6/2010 | Shepard et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 8,053,742 B2 | 11/2011 | Lundquist et al. |
| 8,207,509 B2 | 6/2012 | Lundquist et al. |
| 8,274,040 B2 | 9/2012 | Zhong et al. |
| 8,278,728 B2 | 10/2012 | Murshid |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,502,169 B2 | 8/2013 | Rigneault et al. |
| 8,618,507 B1 | 12/2013 | Lundquist et al. |
| 9,029,802 B2 | 5/2015 | Lundquist et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,060 B2 | 3/2017 | Chen et al. |
| 9,658,161 B2 | 5/2017 | Saxena et al. |
| 9,666,748 B2 | 5/2017 | Leobandung |
| 9,719,138 B2 | 8/2017 | Zhong et al. |
| 9,765,395 B2 | 9/2017 | Goldsmith |
| 9,946,017 B2 | 4/2018 | Saxena et al. |
| 10,018,764 B2 | 7/2018 | Grot et al. |
| 10,090,429 B2 | 10/2018 | Leobandung |
| 10,138,515 B2 | 11/2018 | Fehr et al. |
| 10,280,457 B2 | 5/2019 | Zhong et al. |
| 10,310,178 B2 | 6/2019 | Saxena et al. |
| 10,487,356 B2 | 11/2019 | Lundquist et al. |
| 10,578,788 B2 | 3/2020 | Grot et al. |
| 10,655,172 B2 | 5/2020 | Rank et al. |
| 10,724,090 B2 | 7/2020 | McCaffrey et al. |
| 2002/0182716 A1 | 12/2002 | Weisbuch et al. |
| 2003/0174992 A1 | 9/2003 | Levene et al. |
| 2010/0065726 A1 | 3/2010 | Zhong et al. |
| 2011/0257040 A1 | 10/2011 | Turner et al. |
| 2013/0116153 A1 | 5/2013 | Bowen et al. |
| 2015/0141267 A1 | 5/2015 | Rothberg et al. |
| 2016/0084761 A1* | 3/2016 | Rothberg ........... G01N 21/6454 506/4 |
| 2017/0146479 A1 | 5/2017 | Levine et al. |
| 2017/0350818 A1* | 12/2017 | Rothberg ........... G01N 21/6454 |
| 2019/0292590 A1 | 9/2019 | Zhong et al. |
| 2020/0171484 A1 | 6/2020 | Chen et al. |

OTHER PUBLICATIONS

Hale, Fibre Optic Sensors using Adiabatically Tapered Single Mode Fibres. Dissertation submitted to the University of Cambridge. Feb. 1994. 209 pages.

Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.

Taitt et al., Evanescent wave fluorescence biosensors. Biosens Bioelectron. Jun. 2005;20(12):2470-87. Epub Dec. 8, 2004.

International Search Report and Written Opinion dated Nov. 22, 2019 for International Application No. PCT/US2019/048836.

Invitation to Pay Additional Fees dated Jan. 13, 2020 for International Application No. PCT/US2019/052994.

International Search Report and Written Opinion dated Mar. 19, 2020 for International Application No. PCT/US2019/052994.

Laermer, Micromachining Technologies in MEMS. In: Handbook of Silicon Based MEMS Materials and Technologies. Sep. 2015. Deans. Part IV:452.

\* cited by examiner

SAMPLE WELL FABRICATION TECHNIQUES AND STRUCTURES FOR INTEGRATED SENSOR DEVICES

CROSS-REFERENCE TO RELATED APPLICATIONS

This application claims the benefit under 35 U.S.C. § 119(e) of U.S. Provisional Patent Application Ser. No. 62/724,206, titled "SAMPLE WELL FABRICATION TECHNIQUES AND STRUCTURES FOR INTEGRATED SENSOR DEVICES", and filed on Aug. 29, 2018, which is incorporated by reference herein in its entirety.

BACKGROUND

Field

The present application relates generally to biological sequencing and, more specifically to sample well fabrication techniques and associated structures for integrated sensor devices that may be used in conjunction with sequencing machines.

Related Art

Sequencing of nucleic acids (e.g., deoxyribonucleic acid (DNA), ribonucleic acid (RNA)) includes identifying individual nucleotides in a target nucleic acid. Some nucleic acid sequencing methods include identifying individual nucleotides as they are incorporated into a nucleic acid strand complementary to the target nucleic acid. The series of nucleotides for the complementary strand identified during the sequencing process may then allow for identification of the nucleotide sequence for the target nucleic acid strand.

Detection and analysis of biological samples may be performed using biological assays ("bioassays"). Bioassays conventionally involve large, expensive laboratory equipment requiring research scientists trained to operate the equipment and perform the bioassays. Moreover, bioassays are conventionally performed in bulk such that a large amount of a particular type of sample is necessary for detection and quantitation.

Some bioassays are performed by tagging samples with luminescent markers that emit light of a particular wavelength. The markers are illuminated with a light source to cause luminescence, and the luminescent light is detected with a photodetector to quantify the amount of luminescent light emitted by the markers. Bioassays using luminescent markers conventionally involve expensive laser light sources to illuminate samples and complicated luminescent detection optics and electronics to collect the luminescence from the illuminated samples.

SUMMARY

Some embodiments are directed to a method of forming an integrated device. The method comprises: forming a metal stack over a cladding layer; forming an aperture in the metal stack; forming first spacer material within the aperture; and forming a sample well by removing some of the cladding layer to extend a depth of the aperture into the cladding layer, wherein at least one portion of the first spacer material is in contact with at least one layer of the metal stack.

In some embodiments, forming the metal stack further comprises forming the metal stack on the cladding layer. In some embodiments, forming the first spacer material further comprises forming the first spacer material over the metal stack and at a bottom surface of the aperture. In some embodiments, forming the sample well further comprises performing a first directional etch to remove at least some of the first spacer material disposed on a top surface of the metal stack and on a bottom surface of the aperture. In some embodiments, the first spacer material includes at least one material configured to reduce formation of metal fluoride residue during an etch process used in forming the sample well. In some embodiments, the first spacer material includes at least one material configured to reduce formation of metal fluoride residue on at least one metal layer of the metal stack during an etch process used in forming the sample well. In some embodiments, the at least one portion of the first spacer material is disposed at an undercut region of the metal stack. In some embodiments, the metal stack comprises at least one aluminum containing layer and at least one titanium containing layer.

In some embodiments, the first spacer material is formed by plasma enhanced chemical vapor deposition (PECVD). In some embodiments, the first spacer material includes at least one silicon material. In some embodiments, the first spacer material comprises one or more layers selected from the group of: amorphous silicon ($\alpha$-Si), $SiO_2$, SiON, SiN, and silicon alloy. In some embodiments, the first spacer material is formed by atomic layer deposition (ALD). In some embodiments, the first spacer material comprises one or more layers selected from the group of: $TiO_2$, $Al_2O_3$, $SiO_2$, $HfO_2$, TiN, $Ta_2O_5$, and $ZrO_2$. In some embodiments, the cladding layer comprises $SiO_2$.

In some embodiments, the method further comprises: forming second spacer material into the sample well; and removing at least some of the second spacer material at a bottom surface of the sample well to expose a portion of the cladding layer, wherein at least one portion of the second spacer material is in contact with one or more of the metal stack, the at least one portion of the first spacer material, and the cladding later. In some embodiments, forming the second spacer material further comprises forming the second spacer material over the metal stack. In some embodiments, removing the at least some of the second spacer material further comprises performing a directional etch to remove second spacer material disposed on a top surface of the metal stack and on the bottom surface of the sample well. In some embodiments, the directional etch comprises a fluorocarbon based etch. In some embodiments, the second spacer material is formed by atomic layer deposition (ALD). In some embodiments, the second spacer material comprises one or more layers selected from the group of: $TiO_2$, $Al_2O_3$, $HfO_2$, $ZrO_2$, and $Ta_2O_5$.

Some embodiments are directed to a method of forming an integrated device. The method comprises: forming a metal stack over a cladding layer; forming a dielectric layer over the metal stack; forming an aperture in the metal stack by forming an opening in the dielectric layer and using the dielectric layer as a mask in removing a portion of the metal stack; and forming a sample well by removing a portion of the cladding layer, wherein at least a portion of dielectric layer is removed while forming the sample well.

In some embodiments, forming the metal stack further comprises forming the metal stack on the cladding layer. In some embodiments, forming the dielectric material further comprises forming the dielectric layer on the metal stack. In some embodiments, forming the aperture further comprises etching the opening in the dielectric layer and using the dielectric layer as an etch mask to form the aperture in the metal stack. In some embodiments, forming the sample well further comprises etching the cladding layer and the dielectric layer simultaneously. In some embodiments, the metal stack comprises at least one aluminum containing layer and at least one titanium containing layer. In some embodiments, the cladding layer comprises SiO2.

In some embodiments, the method further comprises: forming a spacer layer over the metal stack and into the sample well; and performing a directional etch to remove portions of the spacer layer disposed on a top surface of the metal stack and on a bottom surface of the sample well to expose a portion of the cladding layer; wherein at least one portion of the spacer layer forms at least one sidewall of the sample well.

In some embodiments, the spacer layer is formed by atomic layer deposition (ALD). In some embodiments, the spacer layer comprises one or more layers selected from the group of: $TiO_2$, $Al_2O_3$, $HfO_2$, $ZrO_2$, and $Ta_2O_5$. In some embodiments, forming the sample well further comprises substantially removing the dielectric layer. In some embodiments, the integrated device after forming the sample well does not include the dielectric layer. In some embodiments, the dielectric layer comprises one or more selected from the group of: amorphous silicon ($\alpha$-Si), $SiO_2$, SiON, SiN, and silicon alloy.

Some embodiments are directed to an integrated device comprising: a cladding layer; a metal stack formed over the cladding layer and having at least one undercut region; a sample well extending through the metal stack proximate to the at least one undercut region and into the cladding layer; and a first spacer material filling the at least one undercut region.

In some embodiments, the first spacer material forms at least one sidewall of the sample well. In some embodiments, the first spacer material comprises one or more selected from the group of: amorphous silicon ($\alpha$-Si), $SiO_2$, SiON, and SiN. In some embodiments, the first spacer material comprises one or more selected from the group of: $TiO_2$, $Al_2O_3$, $HfO_2$, TiN, $ZrO_2$, and $Ta_2O_5$. In some embodiments, the metal stack comprises at least one layer including aluminum and at least one layer including titanium. In some embodiments, the cladding layer comprises $SiO_2$.

In some embodiments, the integrated device further comprises a second spacer material in contact with one or more of the metal stack, the first spacer material, and the cladding layer. In some embodiments, the second spacer material forms at least one sidewall of the sample well. In some embodiments, the second spacer material comprises one or more layers selected from the group of: $TiO_2$, $Al_2O_3$, $HfO_2$, $ZrO_2$, and $Ta_2O_5$. In some embodiments, the metal stack comprises a first layer formed over a second layer, and the undercut region is formed in the second layer.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
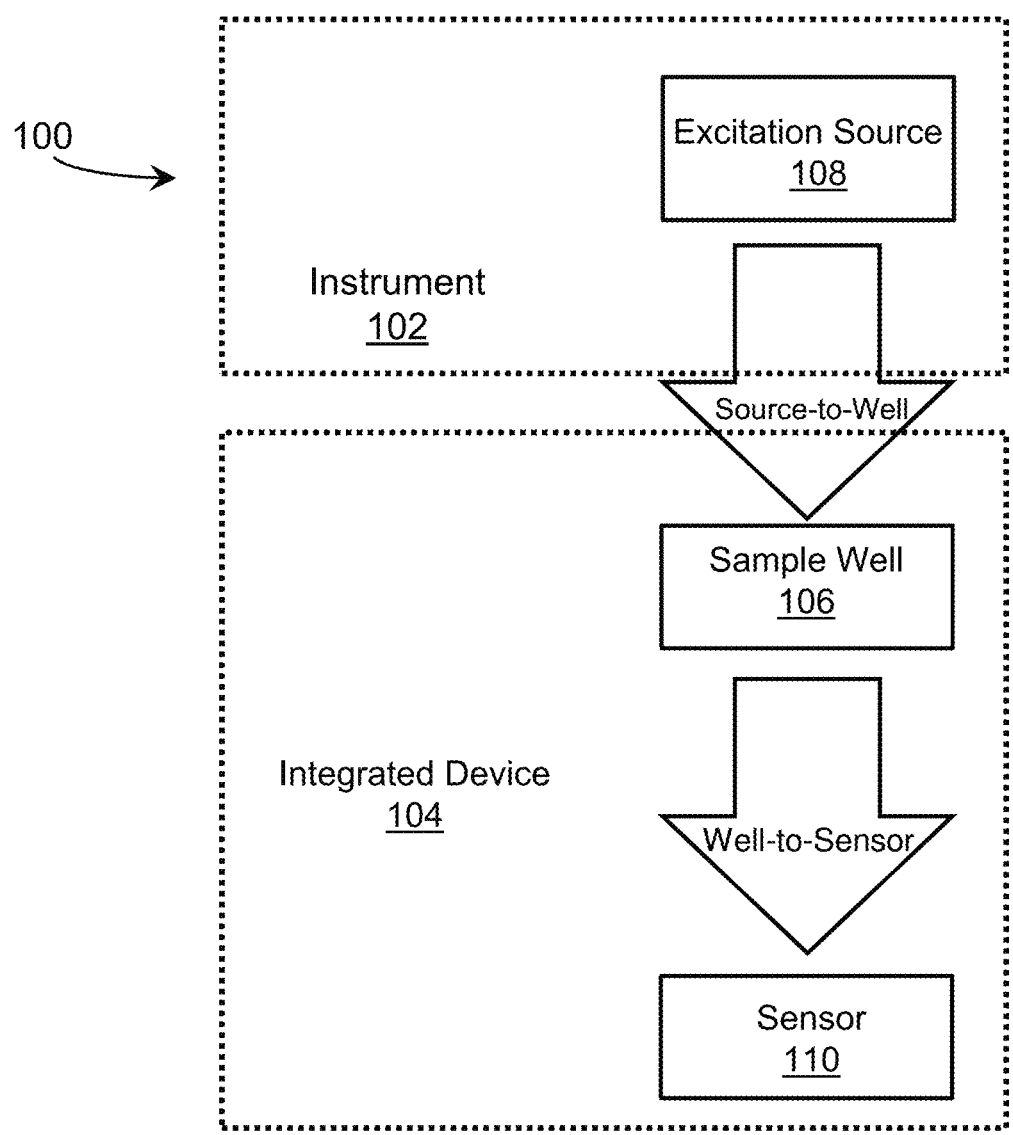
FIG. 1 is a schematic diagram of an exemplary sequencing system, in accordance with some embodiments of the technology described herein.

The techniques described herein relate to sequencing biological molecules, include nucleic acids, such as DNA and RNA, and amino acid sequences, such as peptides or proteins. In particular, these techniques may be used for automatically identifying nucleotides or amino acids based upon data acquired from a sensor. In the context of nucleic acid sequencing, the sequencing may allow for the determination of the order and position of nucleotides in a target nucleic acid. Similarly, for protein or peptide sequencing, the sequencing may allow for the determination of the order and position of amino acids in a protein or peptide molecule. Some nucleic acid sequencing methods are based on sequencing by synthesis, in which the identity of a nucleotide is determined as the nucleotide is incorporated into a newly synthesized strand of nucleic acid that is complementary to the target nucleic acid. During sequencing, a polymerizing enzyme (e.g., DNA polymerase) may couple (e.g., attach) to a priming location of a target nucleic acid molecule and add or incorporate nucleotides to the primer via the action of the polymerizing enzyme, which can be generally referred to as a primer extension reaction.

Each nucleotide may be associated with a luminescent molecule (e.g., fluorophore) that emits light in response to excitation, and which is used to label each type of nucleotide to discriminate among the different types of nucleotides. For example, a set of four labels may be used to label the nucleobases present in DNA such that each marker of the set is associated with a different nucleobase, e.g., a first label being associated with adenine (A), a second label being associated with cytosine (C), a third label being associated with guanine (G), and a fourth label being associated with thymine (T). A label may be coupled to a nucleotide through bonding of the label to the nucleotide either directly or indirectly via a linker molecule.

As the primer extension reaction occurs, a nucleotide and its respective luminescent label are retained by the polymerizing enzyme during incorporation of the nucleotide into the synthesized complementary nucleic acid. The luminescent label can be excited by pulses of light during the period in which the nucleotide is incorporated into the synthesized nucleic acid and emits light characteristic of the label. In some embodiments, the label is attached, either directly or indirectly through a linker molecule, to a terminal phosphate of a nucleotide such that the label is detached or released from the nucleotide via the action of the polymerizing enzyme during incorporation of the nucleotide (e.g., cleavage of a phosphate bond). Sensing and analyzing the light emitted by the luminescent label in response to the excitation can allow identifying the nucleotide that was incorporated. As the primer extension reaction occurs, excitation, sensing and analysis is performed for each subsequent nucleotide added to the synthesized nucleic acid. The sequence of the target nucleic acid can be determined from the complementary sequence of the synthesized nucleic acid.

The light emitted by the luminescent label may have a number of characteristics that can be used to distinguish the label from other labels, and thus identify a nucleotide. These characteristics include intensity (e.g., probability of emitting light), a temporal characteristic (e.g., rate of decay of the probability of photon emission after excitation, pulse duration for incorporation and/or interpulse duration before and/or after incorporation), a spectral characteristic (e.g., wavelength(s) of light emitted), or any combination thereof. The light emitted by the luminescent label may be detected by a photodetector that can detect one of more of these characteristics. An example of a suitable photodetector is described in U.S. patent application Ser. No. 14/821,656 entitled "INTEGRATED DEVICE FOR TEMPORAL BINNING OF RECEIVED PHOTONS," which is hereby incorporated by reference in its entirety. As described therein, the photodetector may have the capability of detecting the arrival times of photons, which can allow for determining temporal characteristics of the light emitted by the labels. Detecting temporal characteristics of the emitted light can in turn allow for discriminating between labels that emit light with different temporal characteristics. One example of a temporal characteristic is luminance lifetime. A luminescent molecule, such as a fluorophore, may emit photons in response to excitation. The probability of the luminescent molecule emitting a photon decreases with time after the excitation occurs. The rate of decay in the probability may be exponential. The "lifetime" is characteristic of how fast the probability decays over time. A fast decay is said to have a short lifetime, while a slow decay is said to have a long lifetime. Detecting temporal characteristics of the light emitted by luminescent molecules can allow for distinguishing luminescent molecules that have different lifetimes. Labeling different nucleotides with luminescent molecules having different lifetimes can allow for distinguishing between the nucleotides based upon a temporal characteristic of the light detected.

The photodetector described in the aforementioned U.S. patent application Ser. No. 14/821,656 can detect the time of arrival of photons with nanosecond or picosecond resolution, and can time-bin the arrival of incident photons. Since the emission of photons is probabilistic, the label may be excited a plurality of times and any resulting photon emissions may be time-binned. Performing such a measurement a plurality of times allows populating a histogram of times at which photons arrived after an excitation event. This information can be analyzed to calculate a temporal characteristic of the emitted light, which can allow for distinguishing the label from another label based on the temporal characteristic.

A compact, high-speed apparatus for performing detection and quantitation of single molecules or particles may reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, access to essential diagnostic tests that could dramatically improve their health and well-being. For example, embodiments described herein may be used for diagnostic tests of blood, urine and/or saliva that may be used by individuals in their home, or by a doctor in a remote clinic in a developing country.

A pixelated sensor device with a large number of pixels (e.g., hundreds, thousands, millions or more) allows for the detection of a plurality of individual molecules or particles in parallel. The molecules may be, by way of example and not limitation, proteins and/or DNA. Moreover, a high-speed device that can acquire data at more than one hundred frames per second allows for the detection and analysis of dynamic processes or changes that occur over time within the sample being analyzed.

One hurdle preventing bioassay equipment from being made more compact is the need to filter the excitation light from causing undesirable detection events at the sensor. Optical filters used to transmit the desired signal light (the luminescence) and sufficiently block the excitation light can be thick, bulky, expensive, and intolerant to variations in the incidence angle of light, preventing miniaturization. However, it has been recognized and appreciated herein that using a pulsed excitation source can reduce the need for such filtering or, in some cases, remove the need for such filters altogether. By using sensors capable of determining the time a photon is detected relative to the excitation light pulse, the signal light can be separated from the excitation light based on the time that the photon is received, rather than the spectrum of the light received. Accordingly, the need for a bulky optical filter is reduced and/or removed in some embodiments.

Luminescence lifetime measurements may also be used to identify the molecules present in a sample. An optical sensor capable of detecting when a photon is detected is capable of measuring, using the statistics gathered from many events, the luminescence lifetime of the molecule being excited by the excitation light. In some embodiments, the luminescence lifetime measurement may be made in addition to a spectral measurement of the luminescence. Alternatively, a spectral measurement of the luminescence may be completely omitted in identifying the sample molecule. Luminescence lifetime measurements may be made with a pulsed excitation source. Additionally, luminescence lifetime measurements may be made using an integrated device that includes the sensor, or a device where the light source is located in a system separate from the integrated device.

It has been recognized and appreciated that integrating a sample well (which may include a nanoaperture) and a sensor in a single integrated device capable of measuring luminescent light emitted from biological samples reduces the cost of producing such a device such that disposable bioanalytical integrated devices may be formed. Disposable, single-use integrated devices that interface with a base instrument may be used anywhere in the world, without the constraint of requiring high-cost biological laboratories for sample analyses. Thus, automated bioanalytics may be brought to regions of the world that previously could not perform quantitative analysis of biological samples. For example, blood tests for infants may be performed by placing a blood sample on a disposable integrated device, placing the disposable integrated device into a small, portable base instrument for analysis, and processing the results by a computer for immediate review by a user. The data may also be transmitted over a data network to a remote location to be analyzed, and/or archived for subsequent clinical analyses.

It has also been recognized and appreciated that a disposable, single-use device may be made more simply and for lower cost by not including the light source on the integrated device. Instead, the light source may include reusable components incorporated into a system that interfaces with the disposable integrated device to analyze a sample.

FIG. 1 is a schematic diagram of an exemplary sequencing system 100, which may be used in conjunction with some embodiments of the sample well fabrication techniques and associated sample well structures described herein. Although these sample well fabrication techniques and sample well structures are described in the context sequencing systems, such as sequencing system 100, it should be appreciated that the techniques described herein may be implemented in fabricating other types of integrated devices, sequencing systems, or other devices where sample wells or other similar structures are desired. It should be appreciated that other arrangements of some or all of the components shown in FIG. 1 may be implemented in some embodiments.

As shown in FIG. 1, sequencing system 100 may include instrument 102, which may be configured to interface with integrated device 104 having multiple sample wells, where an individual sample well 106 is configured to receive a sample from a specimen (not shown) placed on a surface of the integrated device 104. A specimen may contain multiple samples, and in some embodiments, different types of samples. The sample wells may have a suitable size and shape such that at least a portion of the sample wells receive one sample from the specimen. In some embodiments, the number of samples received by individual sample wells may be distributed among the multiple sample wells such that some sample wells contain one sample while others contain zero, or two or more samples.

In some embodiments, a specimen may include multiple single-stranded DNA templates, and individual sample wells on a surface of an integrated device, such as integrated device 104, may be sized and shaped to receive a single-stranded DNA template. Single-stranded DNA templates may be distributed among the sample wells of the integrated device such that at least a portion of the sample wells of the integrated device contain a single-stranded DNA template. The specimen may also contain tagged dNTPs which then enter in the sample well and may allow for identification of a nucleotide as it is incorporated into a strand of DNA complementary to the single-stranded DNA template in the sample well. In such instances, the "sample" may refer to both the single-stranded DNA and the tagged dNTP currently being incorporated by a polymerase. In some embodiments, the specimen may include single-stranded DNA templates and tagged dNTPS may be subsequently introduced to a sample well as nucleotides are incorporated into a complementary strand of DNA within the sample well. In this manner, timing of incorporation of nucleotides may be controlled by when tagged dNTPs are introduced to the sample wells of an integrated device.

Instrument 102 may include excitation source(s) 108, which may be configured to provide excitation energy to integrated device 104. The excitation energy may be directed at least in part by elements of the integrated device towards one or more pixels (not shown in FIG. 1) to illuminate an illumination region within a sample well 106. A label may then emit emission energy when located within the illumination region and in response to being illuminated by excitation energy. In some embodiments, optical components of the instrument 102 and photonics of the integrated device 104 may be configured to direct the excitation energy towards one or more sample wells.

Emission energy emitted by a sample may then be detected by one or more sensors 110 within a pixel of the integrated device 104. Characteristics of the detected emission energy may provide an indication for identifying a label associated with the emission energy. Such characteristics may include any suitable type of characteristic, including an arrival time of photons detected by a sensor, an amount of photons accumulated over time by a sensor, and/or a distribution of photons across two or more sensors. In some embodiments, a sensor 110 may have a configuration that allows for the detection of one or more timing characteristics associated with a sample's emission energy (e.g., fluorescence lifetime). The sensor 110 may detect a distribution of photon arrival times after a pulse of excitation energy propagates through the integrated device, and the distribution of arrival times may provide an indication of a timing characteristic of the sample's emission energy (e.g., a proxy for fluorescence lifetime). In some embodiments, the one or more sensors provide an indication of the probability of emission energy emitted by the label (e.g., fluorescence intensity). In some embodiments, a plurality of sensors may be sized and arranged to capture a spatial distribution of the emission energy. Output signals from the one or more sensors may then be used to distinguish a label from among a plurality of labels, where the plurality of labels may be used to identify a sample within the specimen.

Figure 2:
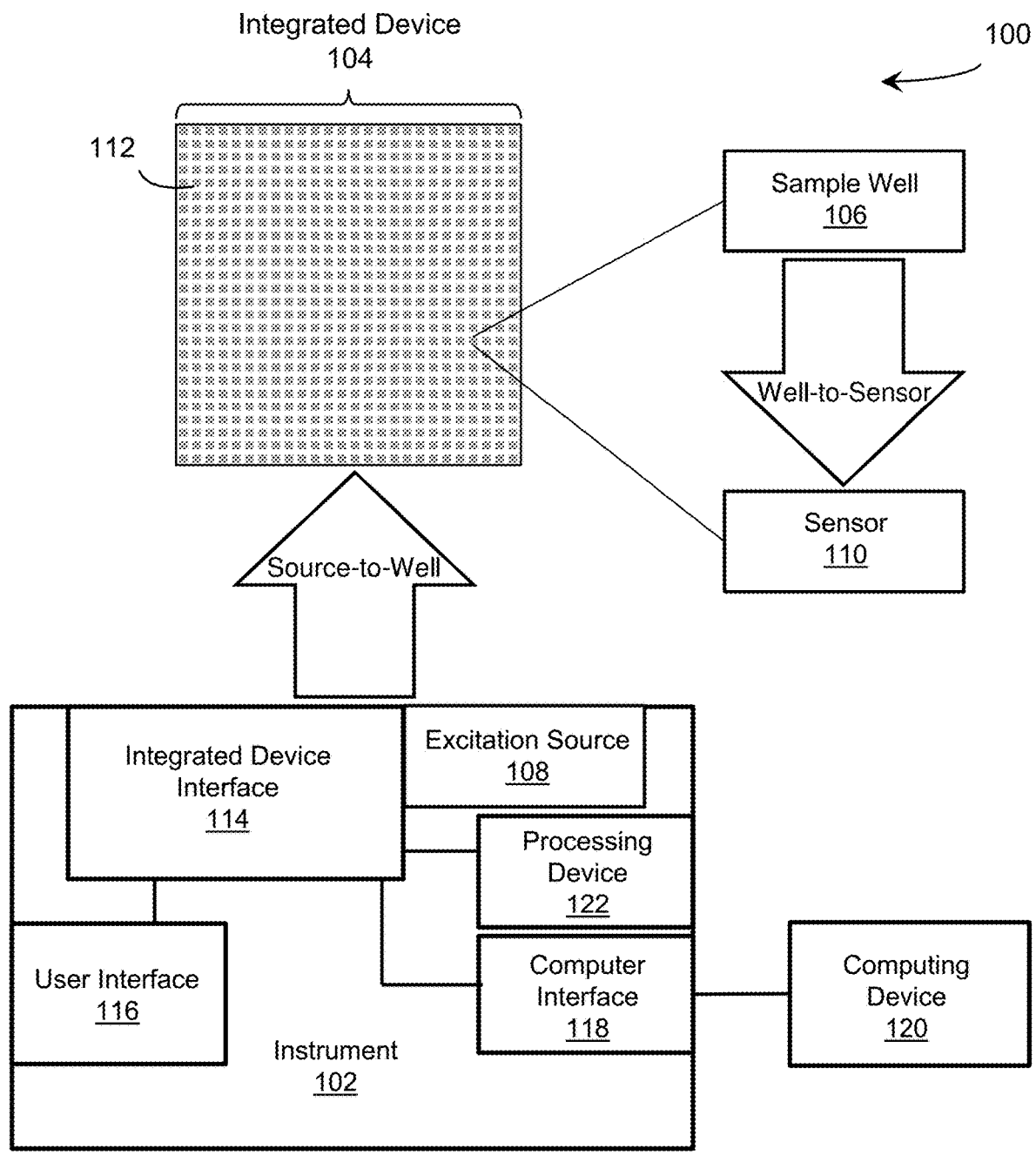
FIG. 2 is a schematic diagram showing further details of the exemplary sequencing system illustrated in FIG. 1.

By way of further illustration, FIG. 2 is a schematic diagram showing further details of the exemplary sequencing system 100 of FIG. 1. Again, the system 100 includes an integrated device 104 that interfaces with an instrument 102. In some embodiments, instrument 102 may include one or more excitation sources 108 integrated as part of instrument 102. In some embodiments, an excitation source 108 may be external to both instrument 102 and integrated device 104, such that instrument 102 may be configured to receive excitation energy from the excitation source(s) 108 and direct it to the integrated device 104. The integrated device 104 may interface with the instrument 102 using any suitable socket for receiving the integrated device 104 and holding it in precise optical alignment with the excitation source(s) 108. The excitation source(s) 108 may also be located within the instrument and configured to provide excitation energy to the integrated device 104. As also illustrated schematically in FIG. 2, the integrated device 104 has multiple individual pixels, where at least a portion of the pixels 112 may perform independent analysis of a sample. Such pixels 112 may be referred to as "passive source pixels" since a pixel receives excitation energy from excitation source(s) 108 separate from the pixel, where the source excites a plurality of pixels. A pixel 112 has both a sample well 106 configured to receive a sample and a sensor 110 for detecting emission energy emitted by the sample in response to illuminating the sample with excitation energy provided by the excitation source 108. A sample well 106 may retain the sample in proximity to a surface of integrated device 104 to provide ease in delivery of excitation energy to the sample and detection of emission energy from the sample.

Optical elements for guiding and coupling excitation energy from the excitation source 108 to the sample well 106 of the integrated device 104 may be incorporated in both the integrated device 104 and the instrument 102. Such source-to-well elements may include, for example, one or more grating couplers located on the integrated device 104 to couple excitation energy to the integrated device 104 and waveguides to deliver excitation energy from instrument 102 to sample wells 106 in pixels 112. In some embodiments, elements located on the integrated device 104 may act to direct emission energy from the sample well 106 towards the sensor 110. According to some embodiments, sample wells 106, a portion of the excitation source-to-well optics, and the sample well-to-sensor optics are located on the integrated device 104, and excitation source(s) 108 and a portion of the source-to-well components are located in the instrument 102. In some embodiments, a single component may play a role in both coupling excitation energy to a sample well 106 and delivering emission energy from the sample well 106 to sensor 110. Examples of suitable components for coupling excitation energy to a sample well and/or directing emission energy to a sensor, to include in an integrated device, are described in U.S. patent application Ser. No. 14/821,688 titled "INTEGRATED DEVICE FOR PROBING, DETECTING AND ANALYZING MOLECULES," and U.S. patent application Ser. No. 14/543,865 titled "INTEGRATED DEVICE WITH EXTERNAL LIGHT SOURCE FOR PROBING, DETECTING, AND ANALYZING MOLECULES," both of which are incorporated by reference in their entirety.

With respect to pixels 112 in the embodiment of FIG. 2, an individual pixel 112 may be associated with its own individual sample well 106 and at least one sensor 110. The pixels 112 may be arranged in an array, and there may be any suitable number of pixels in the array. The number of pixels in integrated device 104 may be in the range of approximately 10,000 pixels to 1,000,000 pixels, or any value or range of values within that range. In some embodiments, the pixels may be arranged in an array of 512 pixels by 512 pixels. Integrated device 104 and instrument 102 may include multi-channel, high-speed communication links (not shown) for handling data associated with large pixel arrays (e.g., more than 10,000 pixels).

As further illustrated in FIG. 2, the instrument 102 may interface with the integrated device 104 through an integrated device interface 114. The integrated device interface 114 may include, for example, components to position and/or align the integrated device 104 to the instrument 102 to facilitate or improve coupling of excitation energy from excitation source(s) 108 to the integrated device 104. The excitation source(s) 108 may be any suitable light source that is arranged to deliver excitation energy to at least one sample well. Examples of suitable excitation sources are described in U.S. patent application Ser. No. 14/821,688, which is incorporated by reference in its entirety. In some embodiments, the excitation source(s) 108 includes multiple excitation sources that are combined to deliver excitation energy to the integrated device 104. Such multiple excitation sources may be configured to produce multiple excitation energies or wavelengths. The integrated device interface 114 may receive readout signals from the sensors 110 in the pixels 112 of the integrated device 104. The integrated device interface 114 may be designed such that the integrated device 104 attaches to the instrument 102 by securing the integrated device 104 to the integrated device interface 114.

Referring still to FIG. 2, the instrument 102 may include a user interface 116 for controlling the operation of instrument 102. The user interface 116 is configured to allow a user to input information into the instrument, such as for example commands and/or settings used to control the functioning of the instrument. In some embodiments, the user interface 116 may include buttons, switches, dials, and a microphone for voice commands. Additionally, the user interface 116 may allow a user to receive feedback on the performance of the instrument and/or integrated device, such as proper alignment and/or information obtained by readout signals from the sensors on the integrated device. In some embodiments, the user interface 116 may provide feedback using a speaker to provide audible feedback, and indicator lights and/or display screen for providing visual feedback. In some embodiments, the instrument 102 includes a computer interface 118 used to connect with an external computing device 120. Any suitable computer interface 118 and computing device 120 may be used. For example, the computer interface 118 may be a USB interface or a FireWire interface. The computing device 120 may be any general purpose computer, such as a laptop or desktop computer. The computer interface 118 facilitates communication of information between the instrument 102 and the computing device 120. Input information for controlling and/or configuring the instrument 102 may be provided through the computing device 120 in communication with the computer interface 118 of the instrument 102. In addition, output information may be received by the computing device 120 through the computer interface 118. Such output information may include, for example, feedback about performance of the instrument 102 and/or integrated device 112 and information from the readout signals of the sensor 110. The instrument 102 may also include a processing device 122 for analyzing data received from the sensor 110 and/or sending control signals to the excitation source(s) 108. In some embodiments, the processing device 122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 110 may be performed by both the processing device 122 and the external computing device 120. In other embodiments, the computing device 120 may be omitted and processing of data from the sensor 110 may be performed entirely by the processing device 122.

Figure 3A:
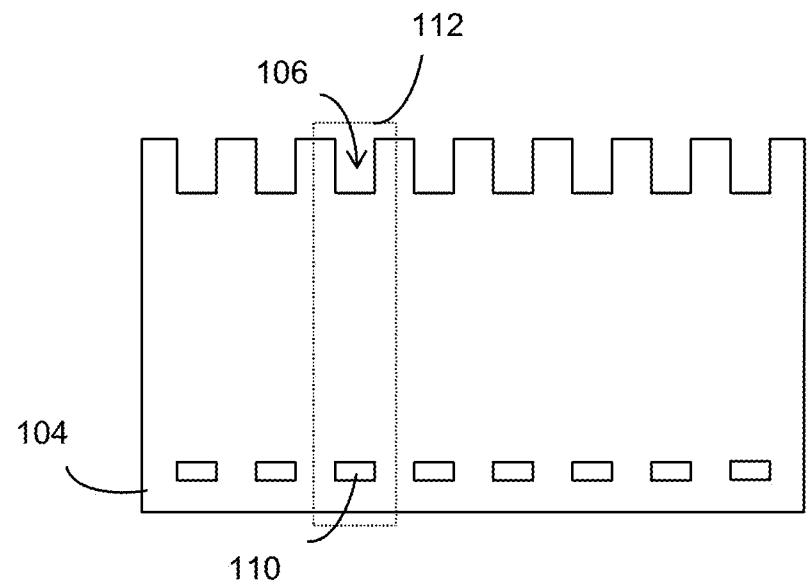
FIG. 3A and FIG. 3B are cross-sectional views illustrating an integrated device, in accordance with some embodiments of the technology described herein.

FIG. 3A is a cross-sectional schematic diagram of the integrated device 104 illustrating a row of pixels 112. Each pixel 112 includes a sample well 106 and a corresponding sensor 110. The sensor 110 may be aligned and positioned to the sample well 106 such that the sensor 110 receives emission energy emitted by a sample (not shown) within sample well 112. Examples of suitable sensors are described in U.S. patent application Ser. No. 14/821,656, which is incorporated by reference in its entirety.

Figure 3B:
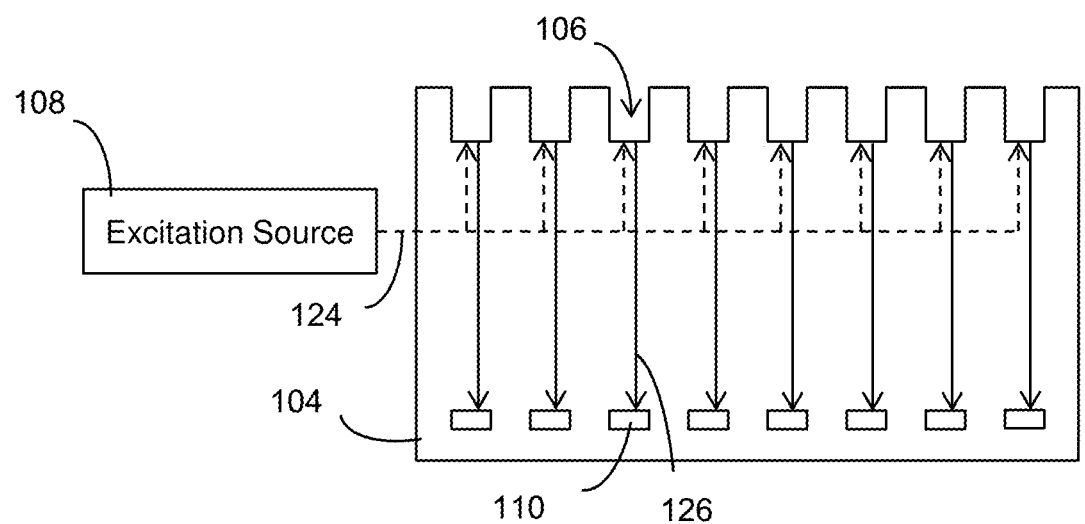

As discussed previously, excitation source(s) 108 coupled to the integrated device 104 may provide excitation energy to one or more pixels of the integrated device 104. By way of further illustration, FIG. 3B is a cross-sectional schematic diagram illustrating coupling of the excitation source(s) 108 to the integrated device 104 to provide excitation energy 124 (the path of which is shown in dashed lines) to the sample wells 106 of the integrated device 104. Components (not shown) located off of the integrated device 104 may be used to position and align the excitation source 108 to the integrated device. Such components may include, for example, optical components such as lenses, mirrors, prisms, apertures, attenuators, and/or optical fibers. Additional mechanical components may also be included in the instrument 102 to allow for control of one or more alignment components. Such mechanical components may include, for example, actuators, stepper motors, and/or knobs.

The integrated device 104 includes components that direct the excitation energy 124 towards pixels 112 therein. More specifically, within each pixel 112, excitation energy is coupled to the sample well 106 associated with the pixel. Although FIG. 3B illustrates excitation energy coupling to each sample well 106 in a row of pixels 112, in some embodiments, it is possible that excitation energy may not couple to all of the pixels 112 in a given row. In some embodiments, excitation energy may couple to a portion of pixels 112 or sample wells 106 in a row of pixels 112 of the integrated device 104. The excitation energy 124 may illuminate a sample located within a sample well 106. The sample may reach an excited state in response to being illuminated by the excitation energy. When a sample is in an excited state, the sample may emit emission energy 126 as shown in FIG. 3B, which emission energy 126 may in turn be detected by a sensor 110. In some embodiments, the sensor 110 may include multiple sub-sensors.

A sample to be analyzed may be introduced into the sample well 106 of pixel 112. The sample may be a biological sample or any other suitable sample, such as a chemical sample. Further, the sample may include multiple molecules and the sample well 106 may be configured to isolate a single molecule. In some instances, the dimensions of the sample well 106 may act to confine a single molecule within the sample well, thereby allowing measurements to be performed on the single molecule. An excitation source 108 may be configured to deliver excitation energy into the sample well 106, so as to excite the sample or at least one luminescent marker attached to the sample or otherwise associated with the sample while it is within an illumination area within the sample well 106.

When an excitation source delivers excitation energy to a sample well, at least one sample within the well may luminesce, and the resulting emission may be detected by a sensor 110. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

One or more components of the integrated device 104 may direct emission energy towards a sensor 110. The emission energy or energies may be detected by the sensor 110 and converted to at least one electrical signal. The electrical signals may be transmitted along conducting lines in the circuitry of the integrated device 104 connected to the instrument 102 through the integrated device interface 114, such as already described in connection with FIG. 2. The electrical signals may be subsequently processed and/or analyzed by a suitable computing device either located on the instrument 102 or off the instrument 102, such as computing device 120 and/or the processing device 122 shown in FIG. 2.

In operation, parallel analyses of samples within the sample wells are carried out by exciting the samples within the wells using the excitation source(s) and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

In some embodiments, a sample may be labeled with one or more markers, and emission associated with the one or more markers is discernable by the instrument. For example, the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor.

A sample may contain multiple types of molecules and different luminescent markers may uniquely associate with a molecule type. During or after excitation, the luminescent marker may emit emission energy. One or more properties of the emission energy may be used to identify one or more types of molecules in the sample. Properties of the emission energy used to distinguish among types of molecules may include a fluorescence lifetime value, intensity, and/or emission wavelength. A sensor may detect photons, including photons of emission energy, and provide electrical signals indicative of one or more of these properties. In some embodiments, electrical signals from a sensor may provide information about a distribution of photon arrival times across one or more time intervals. The distribution of photon arrival times may correspond to when a photon is detected after a pulse of excitation energy is emitted by an excitation source. A value for a time interval may correspond to a number of photons detected during the time interval. Relative values across multiple time intervals may provide an indication of a temporal characteristic of the emission energy (e.g., lifetime). Analyzing a sample may include distinguishing among markers by comparing values for two or more different time intervals within a distribution. In some embodiments, an indication of the intensity may be provided by determining a number of photons across all time bins in a distribution.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof).

A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable labels (e.g., fluorophores).

With respect to the sensor 110, a photodetector may time bin the arrival of incident photons from a label in response to exposing the label to an excitation source 108 (e.g., by a laser pulse). A label may be repeatedly excited, and the arrival of incident photons from the label may be time binned. As an example, during a 10 ms measurement period, laser excitation pulses may be emitted at a frequency of 100 MHz to excite the label. The label may emit a photon with a low probability (e.g., 1 photon emission in 10,000 excitations). If the label is excited a number of times (e.g., 1 million times) within a 10 ms period, approximately 100 photons may be received. In some instances, a label may not become excited after exposure to an excitation source and not emit a photon after an excitation event, which may contribute to the low probability of emission. As discussed above, the arrival times of the incident photons with respect to the excitation may be time-binned. As such, a photodetector may provide signals representing the number of photons in each time bin. In some embodiments, sensor 110 may be configured to detect a characteristic wavelength, or range of wavelengths, of the emitted light. In such embodiments, the characteristic wavelength or range of wavelengths may be used in distinguishing among different labels. In some embodiments, sensor 110 may be configured to detect an intensity of the emitted light, which may be used in distinguishing among different labels.

Some embodiments of the present application relate to sample well fabrication techniques and sample well structures that provide selective chemical functionalization, which may allow for a sample, or a component of a sample to be analyze, to be positioned at a bottom surface of a sample well. Certain methods can be used to modify the exposed surfaces of the device to enable selective surface functionalization and to confer anti-corrosive and/or anti-fouling properties on device surfaces, among other advantages. Selective surface modification can involve treating an exposed surface of the device with one or more reagents to form a surface coating, such as a self-assembled monolayer, over the exposed surface of the device. Surface coatings can make the device more capable of withstanding corrosive solutions by protecting the underlying material of the exposed surface, for example, in bioassays that require the use of corrosive solutions or other harsh conditions (e.g., high salt solutions, multiple solution washes, etc.). Surface coatings can also provide a more favorable interface for reagents in a bioassay, such as anti-fouling surface coatings which reduce or eliminate the adherence of reagent components in a biological reaction. Examples of suitable surface coatings and surface modification processes are described in U.S. patent application Ser. No. 15/971,493, titled "SUBSTRATES HAVING MODIFIED SURFACE REACTIVITY AND ANTIFOULING PROPERTIES IN BIOLOGICAL REACTIONS," which is hereby incorporated by reference in its entirety. It should be appreciated that such surface coatings may be implemented in the embodiments of the sample well described herein.

Figure 4:
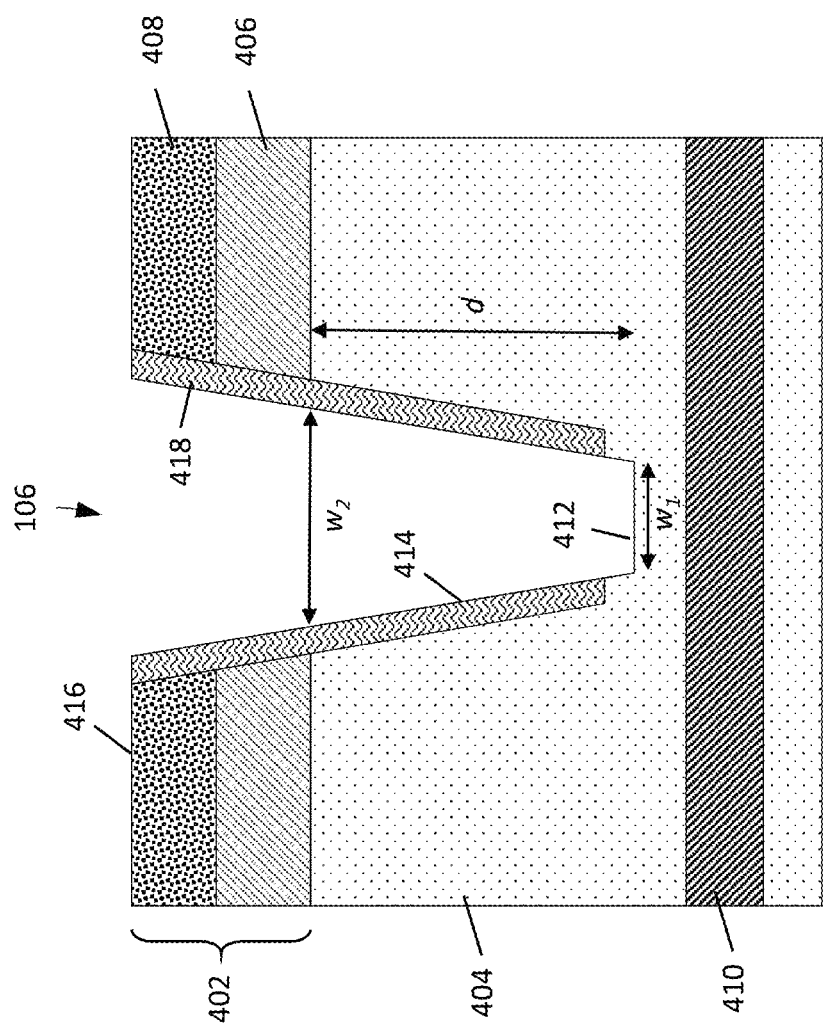
FIG. 4 is a cross-sectional view illustrating a sample well, in accordance with some embodiments of the technology described herein.

FIG. 4 is a cross-sectional view illustrating an exemplary sample well 106, such as those shown in the integrated devices of FIG. 1, FIG. 2, FIG. 3A and FIG. 3B. As shown in FIG. 4, the sample well 106 is defined by an opening formed through a metal stack 402 disposed on a cladding layer 404 (e.g., $SiO_2$). Metal stack 402 may include one or more layers of metal material(s) (e.g., aluminum, titanium, copper). As shown in FIG. 4, some embodiments of metal stack 402 include an aluminum layer 406 positioned proximate to the top of the cladding layer 404 and a titanium nitride layer 408 over the aluminum layer 406.

The aluminum layer 406 may include copper and/or silicon. In some embodiments, the aluminum layer 406 may include less than approximately 2% of copper and/or silicon, and may have a thickness in the range of about 30 nm to 150 nm, or any value or range of values within that range. In some embodiments, the aluminum layer is about 65 nm. The titanium nitride layer 408 may include a layer of titanium in contact with the aluminum layer 406 and have a thickness of in the range of 1 nm to 150 nm, or any value or range of values within that range. In some embodiments, the thickness of titanium nitride layer is approximately 80 nm. For illustrative purposes, FIG. 4 also depicts an exemplary waveguide structure 410 (e.g., silicon nitride) that facilitates delivery of excitation optical energy to the sample well 106.

The depth, d, of the recess formed in the cladding layer 404 defines the distance of light emitted from a label at a bottom surface of sample well 106 to the aluminum layer 406 (e.g., Al—Cu), which may act as a metal reflector for reflecting light, such as emission light. This distance in turn determines the directionality of emission light toward the optical sensor (not shown), which may impact optical collection efficiency. Depth, d, of the recess may be in the range of 100 nm to 500 nm, or any value or range of values in that range. In some embodiments, a depth, d, for the recess is about 300 nm. In some embodiments, the depth, d, for the recess is about 360 nm. In addition, the lateral dimensions (diameter) of the sample well may impact the ability of a DNA template and dye-labelled nucleotides to access, through diffusion, an enzyme that is immobilized at the bottom of the sample well. Generally speaking, larger dimensions improve such access. Furthermore, the lateral dimensions of the sample well 106 may also impact the volume of the illumination region that is illuminated by the waveguide 410. In particular, the dimension $w_1$ at the bottom of the sample well has a significant impact on the volume of the illumination region that is excited, where smaller dimensions result in a smaller volume being excited, which may in turn provide a lower background signal. In some embodiments, sample well 106 has a diameter $w_1$ at the bottom of the recess in the range of 50 nm to 300 nm, or any value or range of values in that range. In some embodiments, sample well 106 has a diameter $w_2$ at the top of cladding layer 404 in the range of 100 nm to 300 nm, or any value or range of values in that range. In some embodiments, sample well 106 has a diameter $w_2$ at the top of cladding layer 404 in the range of 150 nm to 250 nm, or any value or range of values in that range, and a diameter $w_1$ at the bottom of the recess in the range of 75 nm to 200 nm, or any value or range of values in that range. In some embodiments, sample well 106 may have tapered sidewalls, as shown in FIG. 4.

In order to facilitate selective chemical functionalization to immobilize an enzyme at the bottom of the sample well 106, the bottom surface 412 of the sample well 106 should have a different composition than other surfaces (e.g., the sidewalls 414 of the sample well 106 and top surface 416 of the integrated device). As shown in FIG. 4, bottom surface 412 of the sample well may be the material of the cladding layer (e.g., exposed $SiO_2$) and the sidewalls 414 of the sample well 106 may be a spacer material 418. Spacer material 418 may include one or more metal oxides (e.g., $TiO_2$, $Al_2O_3$, $SiO_2$, TiN, $HfO_2$, $ZrO_2$, and $Ta_2O_5$). The top surface 416 of the integrated device may include one or more metal oxide materials formed by oxidation of the top surface of layer 408 (e.g., $TiO_2$ formed by oxidation of TiN).

In some embodiments, it may be desired to have the exposed surfaces of the integrated device (top surface, sample well sidewalls, bottom surface) be substantially stable for particular types of solutions, including those used during operation of the integrated device and during surface functionalization. For example, some solutions that are used for device operation may include high ionic strength aqueous solutions, and the exposed surfaces of the integrated device may be substantially stable when in contact with such solutions for a desired period of time. As another example, some solutions that are used for surface functionalization of the integrated device may include acidic solutions, and the exposed surfaces of the integrated device may be substantially stable when in contact with such solutions for a desired period of time. According to some embodiments where aluminum is included in one or more layers of the integrated device, it may be preferable to have those one or more layers that include aluminum be encapsulated in a final structure, which may improve stability of the surfaces of the integrated device. In addition, it may be desired to have the surfaces of the integrated device be sufficiently clean to enable surface functionalization.

Figure 5:
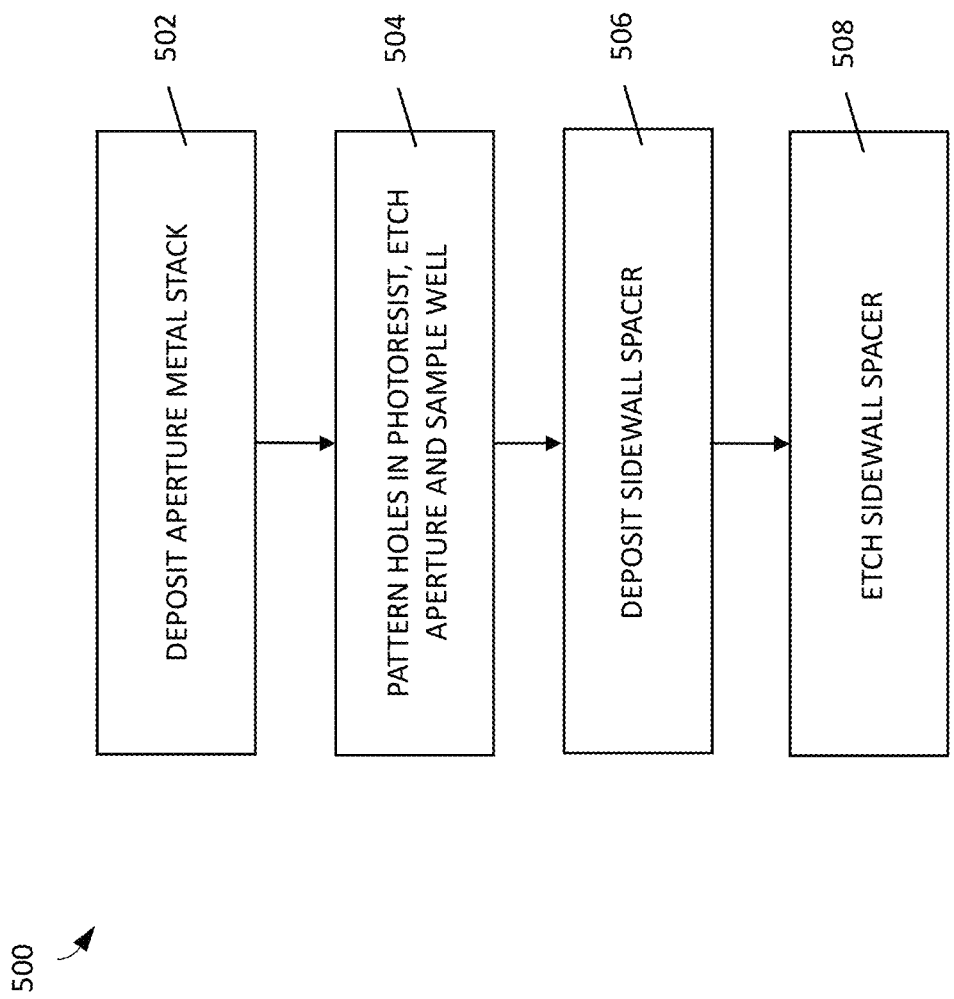
FIG. 5 is a flow diagram illustrating an exemplary process for forming a sample well, in accordance with some embodiments of the technology described herein.
Figure 6:
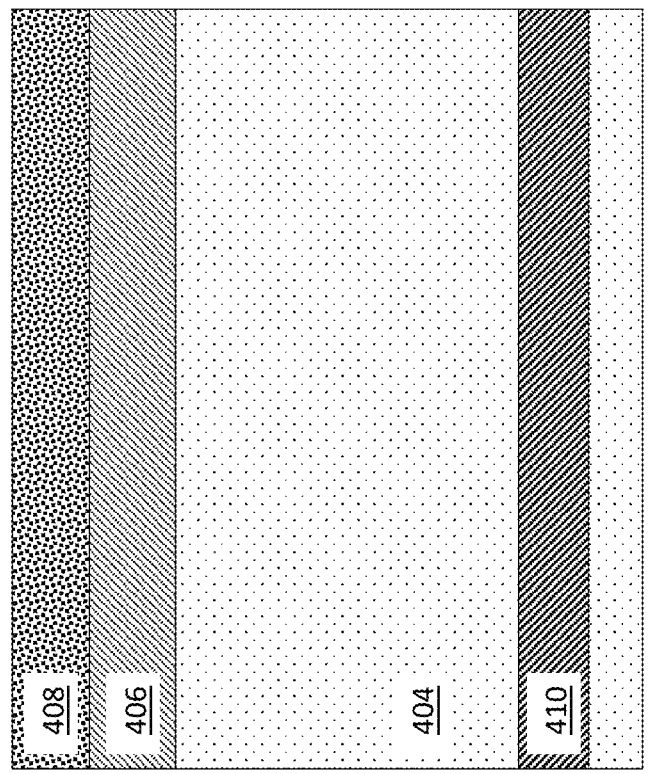

FIG. 5 is a flow diagram illustrating exemplary process 500 for forming a sample well, according to some embodiments. FIGS. 6-11 show cross-sectional views for some of the steps of process 500. For ease of illustration, like elements and components are denoted with like reference numbers in the various figures. Process 500 includes act 502 of depositing an aperture metal stack over one or more layers, such as a cladding layer and a waveguide. As shown in FIG. 6, a metal aperture film stack, which includes an aluminum layer 406 and titanium nitride layer 408 is formed over cladding layer 404 and waveguide 410. In some embodiments, prior to forming the metal aperture film stack a top surface of cladding layer 404 may be planarized using any suitable planarization process (e.g., a CMP process). In some embodiments, aluminum layer 406 may be deposited to have a thickness of about 65 nm and titanium nitride layer 408 may include a titanium layer having a thickness of about 10 nm of Ti and a titanium nitride layer of about 70.

Figure 7:
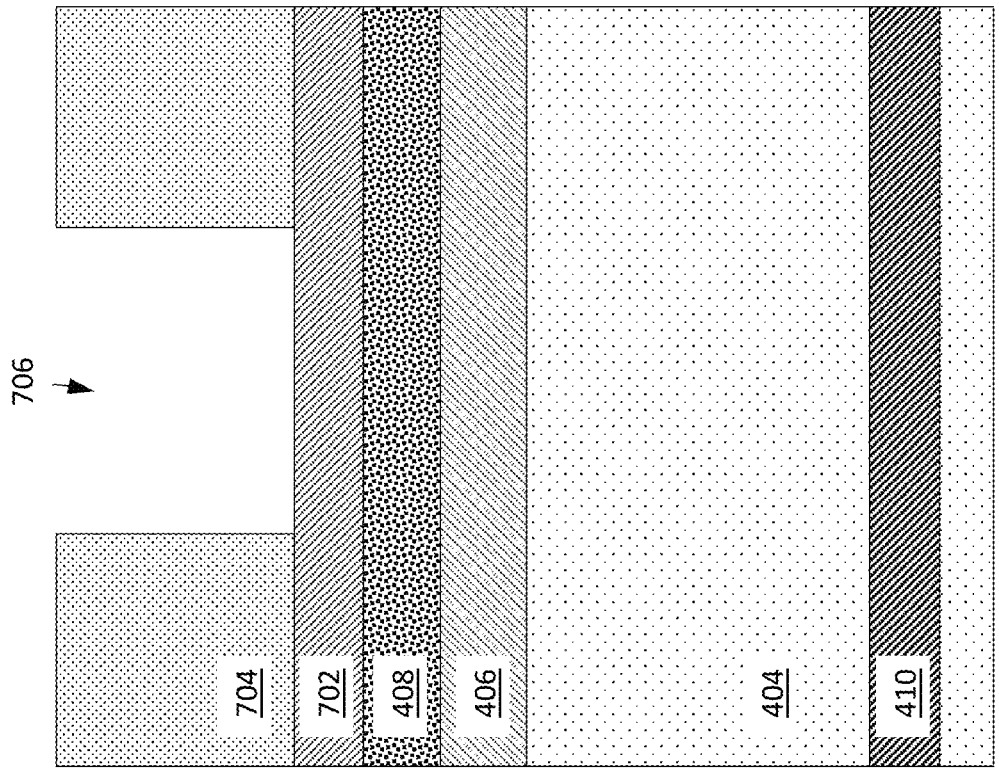
FIGS. 6, 7, 8, 9, 10, and 11 are sequential cross-sectional views illustrating the exemplary process for forming a sample well of FIG. 5.
Figure 9:
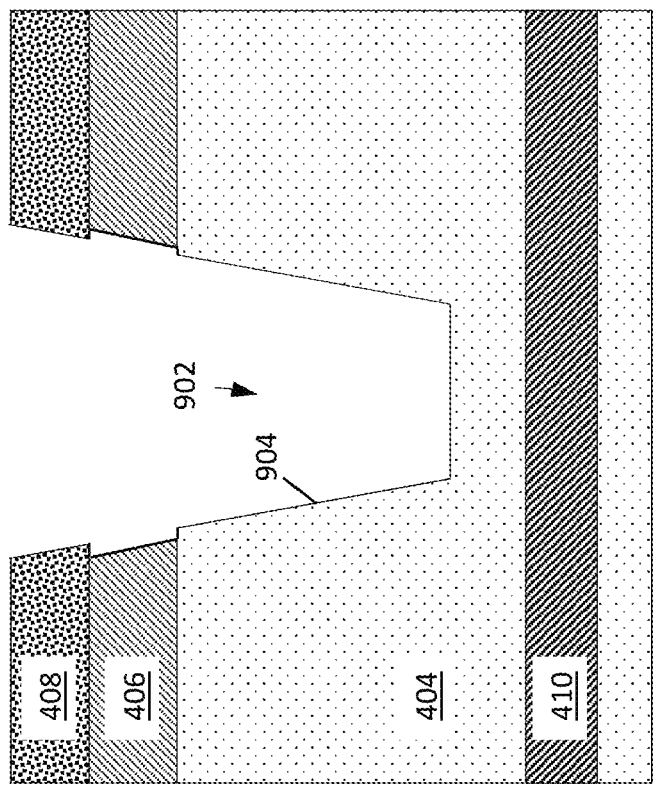
Figure 8:
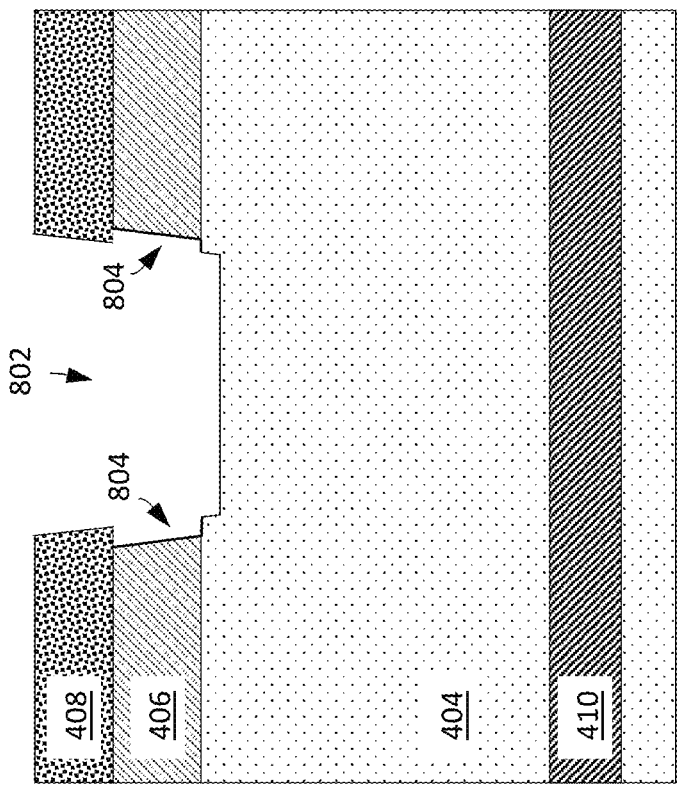

Next, process 500 proceeds with act 504, which involves patterning one or more holes in a photoresist layer over the metal stack and etching an aperture in at least the metal stack. The photoresist layer may facilitate the etching process by defining the aperture in the metal stack. Act 504 may also include forming a sample well extending into a cladding layer under the metal stack. Further details of the patterning of the photoresist layer and etching are shown in FIGS. 7-9. As shown in FIG. 7, a bottom antireflective coating (BARC) layer 702 may first be formed over the titanium nitride layer 408 and photoresist layer 704 is formed over BARC layer 702. A hole 706, corresponding to a location of the resulting sample well, is then patterned in the photoresist layer 704. Patterning of photoresist layer 704 may involve any suitable photolithographic techniques, including photolithographic exposure and development of the photoresist layer 704. Hole 706 may have any suitable size and shape. In some embodiments, hole 706 may have a circular shape and a diameter in the range of 150 nm to 225 nm, or any value or range of values in that range. In further preparation for aperture etching, the BARC layer 702 may be selectively removed using a plasma etching process, or any suitable technique.

As shown in FIG. 8, an etch of the metal stack, which includes layers 406, 408, is performed to define an aperture 802. The etch process used to define the aperture 802 shown in FIG. 8 may be performed by the same process used to remove the BARC layer 702 in FIG. 7, such as for example by a plasma etch process, which may involve using $Cl_2$ and/or $BCl_3$. The plasma etching process may be followed by an $O_2$ ashing step, water rinse and/or post-etch cleaning step. In some embodiments, the plasma etching process may be isotropic and result in undercut regions in one or more layers of metal stack. For example, a Cl-based etch of aluminum may be somewhat isotropic in nature, which may lead to undercut regions 804 in aluminum layer 406. In some embodiments, a wet clean step can contribute to the formation undercut regions in metal stack, such as undercut regions 804.

FIG. 9 shows sample well 902, having sidewalls 904, formed by an etch of cladding layer 404. Oxide material of the cladding layer 404 may be removed through the use of a dry fluorocarbon etch (e.g., $CF_4$, $CHF_3$, $C_4F_8$, $C_3H_2F_6$), followed by an $O_2$ ashing step and post-etch cleaning step. In some embodiments, the dry etching process may occur for a duration of time to achieve a desired etch depth or, alternatively through the use of an etch stop layer (not shown) positioned at a location within the cladding layer 404 to achieve the desired etch depth. In some embodiments one or more sidewalls 904 of the resulting sample well 902 formed by the etching process may be at an angle normal to a top surface of the integrated device, such as shown in FIG. 9. Sidewalls 904 of the sample well 902 may be tapered at an angle in the range of 1° to 15°, with respect to a normal to the top surface of the integrated device. In other words, the sample well 902 may be tapered such that its diameter decreases with increasing depth.

Returning to FIG. 7, the photoresist layer 704 and/or BARC layer 702 may be removed from the metal stack 406, 408 using a plasma removal process (e.g., ashing, cleaning), or any suitable technique. In some embodiments, the photoresist layer 704 and/or BARC layer 702 are removed after etching of metal stack 406, 408 (which is shown in FIG. 8) and prior to etching of the cladding layer 404 (which is shown in FIG. 9). In some embodiments, the photoresist layer 704 and/or BARC layer 702 are removed after etching of both metal stack 406, 408 and top cladding the cladding layer 404.

Figure 10:
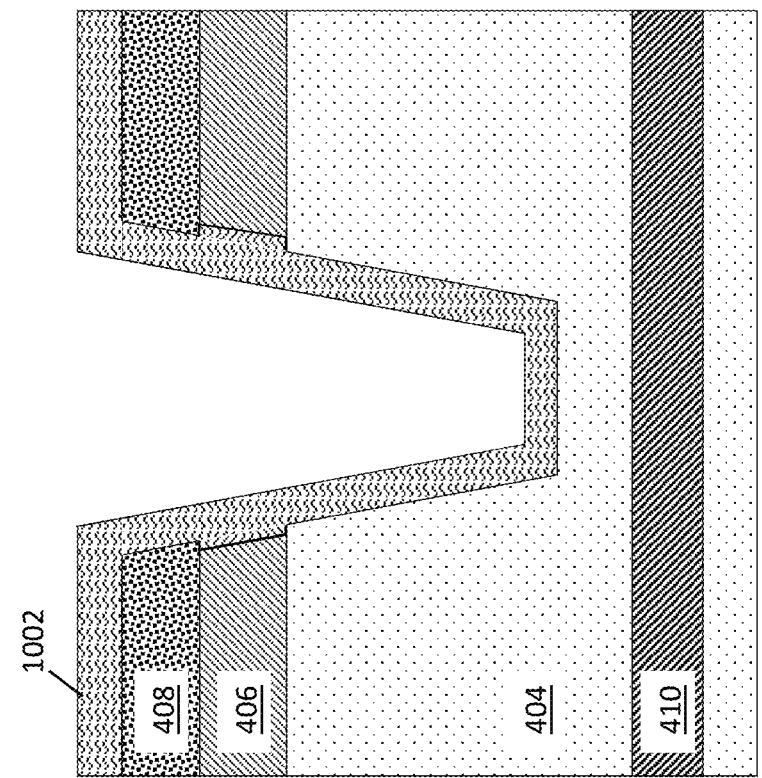

Process 500 proceeds by act 506, which includes depositing spacer material on the sidewall(s) of the sample well. The space material may be deposited in a conformal manner, and may be referred to as "a conformal spacer layer" in some embodiments. As shown in FIG. 10, spacer layer 1002 is deposited in sample well 902, and may contact one or more of cladding layer 404 and metal stack, including layers 406 and 408. Examples of spacer materials that may be used as a spacer layer may include $Al_2O_3$, TiN, $Ta_2O_5$, TaN, $ZrO_2$, $TiO_2$, and $HfO_2$. A thickness of the spacer layer may be in the range of 3 nm to 50 nm, or any value or range of values in that range. In some embodiments, spacer layer 1002 may be a layer of $TiO_2$ having a thickness between about 3 nm to about 30 nm. In some embodiments, spacer layer 1002 may be a layer of $TiO_2$ formed by atomic layer deposition (ALD) at a temperature of about 230° C. and has a thickness of about 12 nm. In some embodiments, conformal spacer layer 1002 may include multiple layers of materials. In such embodiments, the multiple layers of materials may facilitate fabrication, surface functionalization, and/or surface cleaning.

Figure 11:
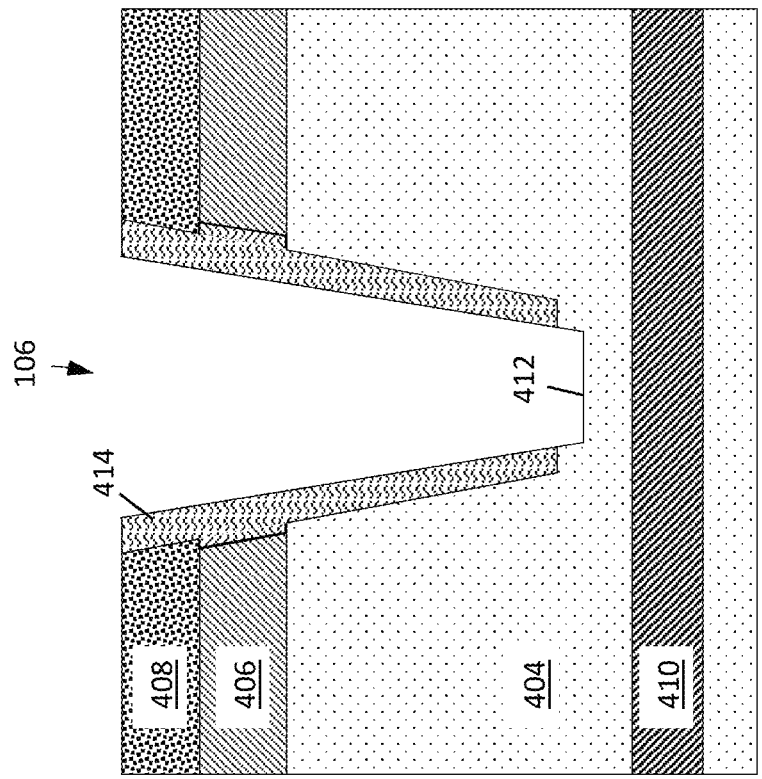

Then, process 500 proceeds by act 508, which includes etching the spacer material. In some embodiments, an anisotropic (directional) etch may be used in etching the spacer material and remove horizontally disposed surfaces of the spacer layer, which may result in the spacer material along vertical surfaces, such as the sidewalls of a sample well. As shown in FIG. 11, an anisotropic etch of spacer layer 1002 removed the horizontal surfaces at the bottom of the sample well and the top surface of the integrated device, such that sidewall spacers 414 are formed in the resulting sample well 106. In addition, bottom surface 412 of sample well 106 is exposed cladding material (e.g., $SiO_2$). In embodiments where the spacer layer includes $TiO_2$, and results in sidewall spacers having $TiO_2$, a fluorocarbon or $BCl_3$ etch chemistry (with $O_2$ and/or air) may be used. In embodiments where the spacer layer includes $Al_2O_3$, and results in sidewall spacers having $Al_2O_3$, a $BCl_3$ etch chemistry (with $Cl_2$ and/or air) may be used. As the bottom surface 412 of the sample well 106 is of a different material than the sidewall spacers 414 and top surface of the integrated device, the resulting structure may provide a different functionality for preferential binding of a sample (not shown) to the bottom surface 412 in comparison to the sidewalls 414 of the sample well. Thus, upon completion of the sample well structure etch, additional processing steps may be performed such as, for example, attachment of biotin species on the bottom surface 412 of the sample well 106 and chip passivation. Examples of additional processing steps that result in modified bottom surface chemistry and passivation are described in U.S. patent application Ser. No. 15/971,493, which is hereby incorporated by reference in its entirety.

Possible side effects of process 500 described above may be the presence of aluminum fluoride (AlF) and other residues on the aperture and sample well sidewalls from a fluorocarbon based etch. Such residues in turn may affect the integrity of the sidewall spacer deposition. In addition, the exposed aluminum of layer 406 may also be subject to other deleterious effects, such as from corrosion or humidity. In addition, for embodiments where the top titanium nitride layer 408 serves as an etch mask for removing the cladding material, it is further possible that edges of the top titanium nitride layer 408 adjacent the aperture (such as aperture 802 shown in FIG. 8) could become eroded during the sample well etch processing and result in exposed aluminum.

Figure 12:
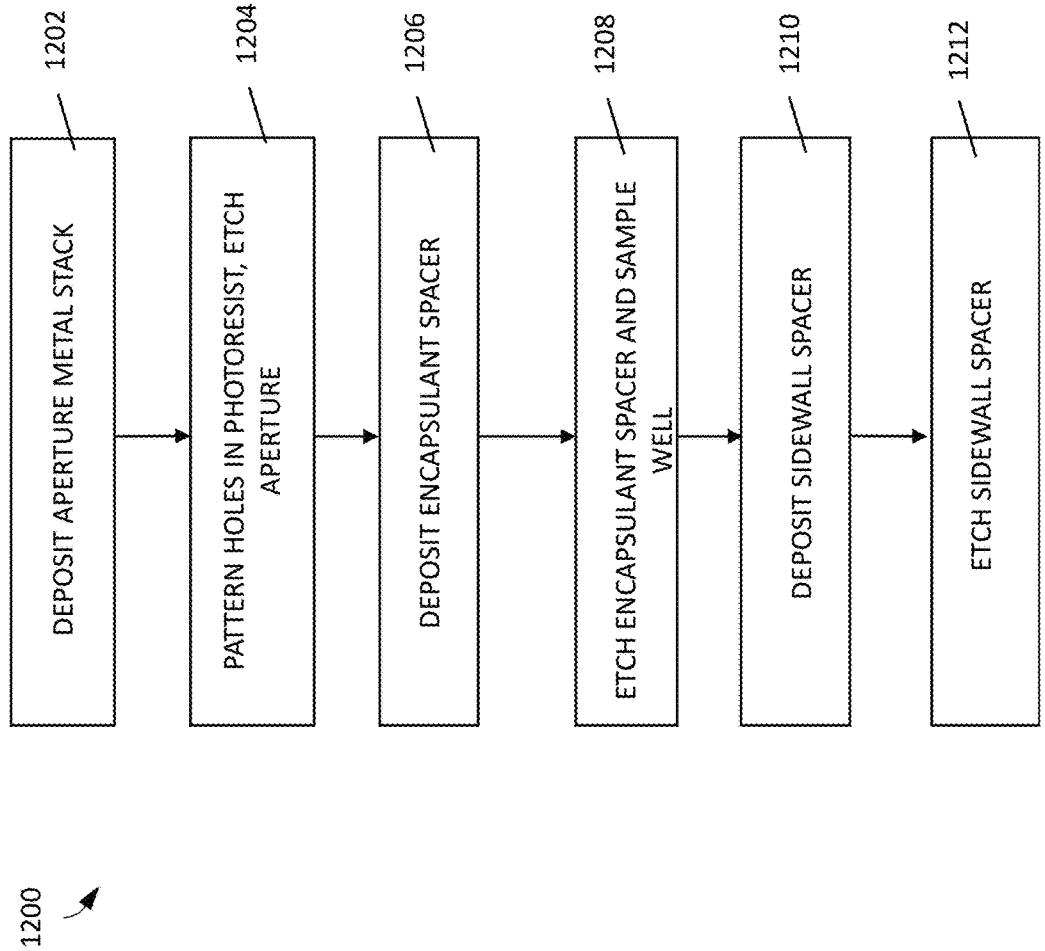
FIG. 12 is a flow diagram illustrating an exemplary process for forming a sample well, in accordance with some embodiments of the technology described herein.
Figure 13:
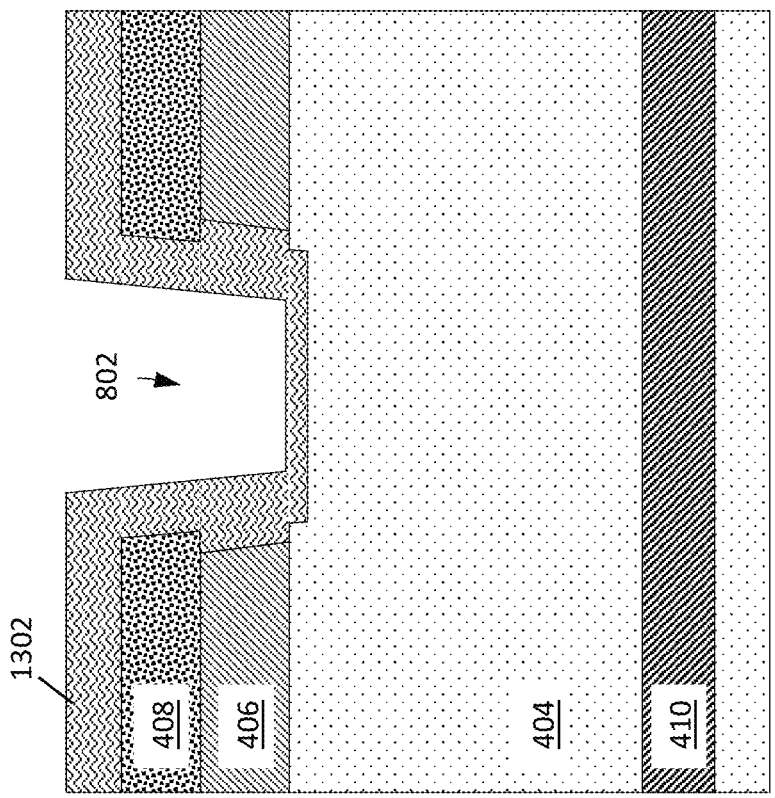

Some embodiments may involve using an encapsulant spacer to protect sidewalls of the aperture metal stack, such as an aluminum layer in the metal stack. FIG. 12 is a flow diagram illustrating exemplary process 1200 for forming a sample well structure. FIGS. 13-16 show cross-sectional views for some of the steps of process 1200. As shown in FIG. 12, the process 1200 begins at act 1202 by depositing a metal stack over one or more layers, such as a cladding layer or a waveguide. Depositing the metal stack may be performed using processes and materials described above in connection with process 500. Process 1200 proceeds to act 1204, which includes etching an aperture into the metal stack by patterning a photoresist material and, in some embodiments, a BARC layer. Etching the aperture into the metal stack may be performed using processes and materials described above in connection with process 500, and shown in FIG. 7 and FIG. 8. FIG. 13 shows etched metal stack 406, 408 over cladding layer 404.

In contrast to the process 500, process 1200 proceeds to act 1206, which involves depositing an encapsulant spacer material within the aperture formed by act 1204. FIG. 13 shows encapsulant spacer material 1302 formed within aperture 802, contacting a surface of cladding layer 404, metal stack 406, 408, and top surface. Encapsulant spacer material 1302 may be any suitable material that acts to protect one or more layers of metal stack 406, 408 during subsequent processing steps, and in particular, may reduce or prevent the formation of metal fluoride residue from subsequent etching of the cladding material 404. The encapsulant spacer material 1302 may include one or more silicon materials. Examples of suitable materials in encapsulant spacer material 1302 may include amorphous silicon (α-Si), $SiO_2$, SiON, SiN, and one or more silicon alloys (e.g., silicon-rich oxide (SRO), silicon-rich nitride (SRN)). In some embodiments, the encapsulant spacer material 1302 may be amorphous silicon (α-Si) deposited by plasma enhanced chemical vapor deposition (PECVD). In other embodiments, the encapsulant spacer material 1302 may be PECVD deposited $SiO_2$, SiON, or SiN. In some embodiments, the encapsulant spacer material 1302 may be an oxide material (e.g., $TiO_2$, $Al_2O_3$, $SiO_2$, $HfO_2$, TiN, $Ta_2O_5$, $ZrO_2$) formed by atomic layer deposition (ALD). In some embodiments, encapsulant spacer material 1302 may include multiple layers of one or more materials. Generally, the encapsulant spacer material 1302 may be deposited in a conformal manner with respect to the top surface of metal layer 408 and the bottom of the aperture 802. In some embodiments, the encapsulant spacer material 1302 may have varying thickness. For example, encapsulant spacer material 1302 may have a larger thickness at locations on the top surface of metal layer 408 than along the bottom of the aperture 802.

Figure 14:
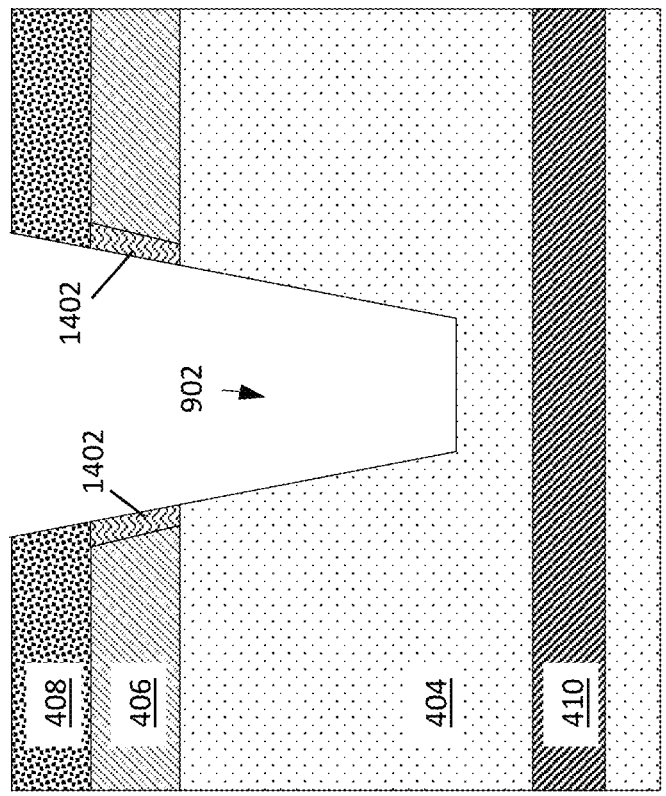
FIGS. 13, 14, 15, and 16 are sequential cross-sectional views illustrating the exemplary process for forming a sample well of FIG. 12.

Process 1200 continues by act 1208, where the encapsulant spacer material is etched and the cladding material is etched to form a sample well. FIG. 14 shows sample well 902 formed by etching encapsulant spacer material and cladding layer 404. In some embodiments, the encapsulant spacer etch and/or the sample well etch may involve a fluorocarbon based etch, such as described above, followed by an $O_2$ ash process and a post-etch clean process. In embodiments where the etch of the encapsulant material and cladding material is substantially an anisotropic, directional etch, one or more portions of the encapsulant spacer material may remain on sidewalls of the metal stack. As shown in FIG. 14, the aluminum layer 406 has one or more undercut regions where encapsulant spacer 1402 remains after the etching to form the sample well. The encapsulant spacer 1402 may advantageously protect the exposed aluminum sidewalls of layer 406. Protection by the encapsulant spacer 1402 may reduce or prevent formation of metal fluoride residues during the sample well etch, which might otherwise be vulnerable to corrosion/humidity or reaction with F, Cl during subsequent etching.

Figure 15:
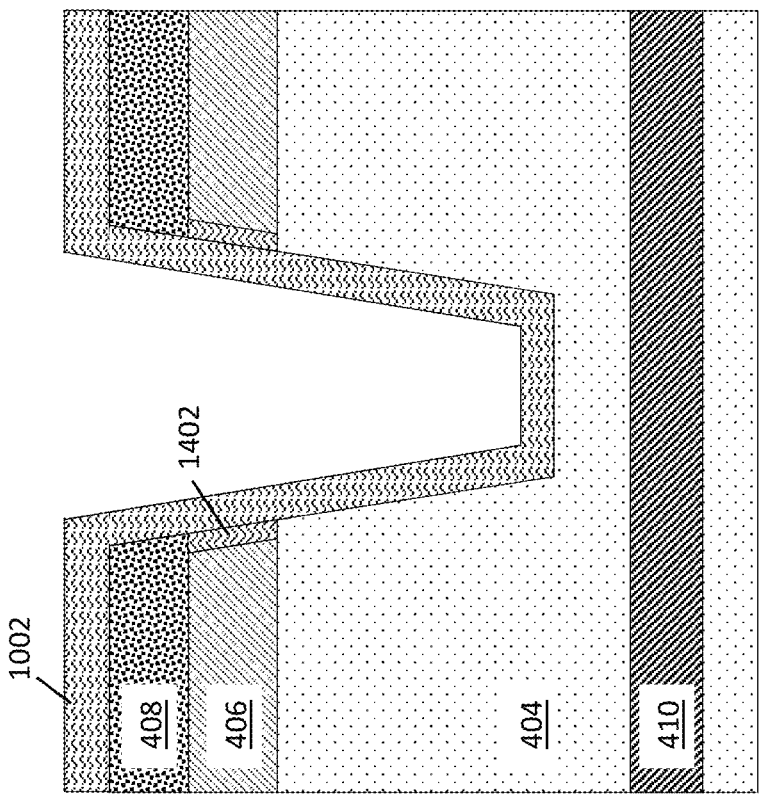

From this point, process 1200 may continue similar to that of process 500. Process 1200 may proceed with act 1210, where a sidewall spacer material is deposited, which may involve using similar materials and processes as described in connection with act 506 of process 500. FIG. 15 shows sidewall spacer material 1002, which contacts encapsulant spacer portions 1402. Examples of spacer materials that may be used to form sidewall spacer material 1002 include $Al_2O_3$, $TiO_2$, TiN, $Ta_2O_5$, TaN, $ZrO_2$ and $HfO_2$. In some embodiments, the sidewall spacer material 1002 may include multiple layers of one or more materials. In some embodiments, the sidewall spacer material 1002 may be a layer of $TiO_2$ formed to a thickness between about 3 nm to about 30 nm. In some embodiments, the sidewall spacer material 1002 may be a layer of $TiO_2$ formed to a thickness of about 12 nm by atomic layer deposition (ALD) at a temperature of about 230° C.

Figure 16:
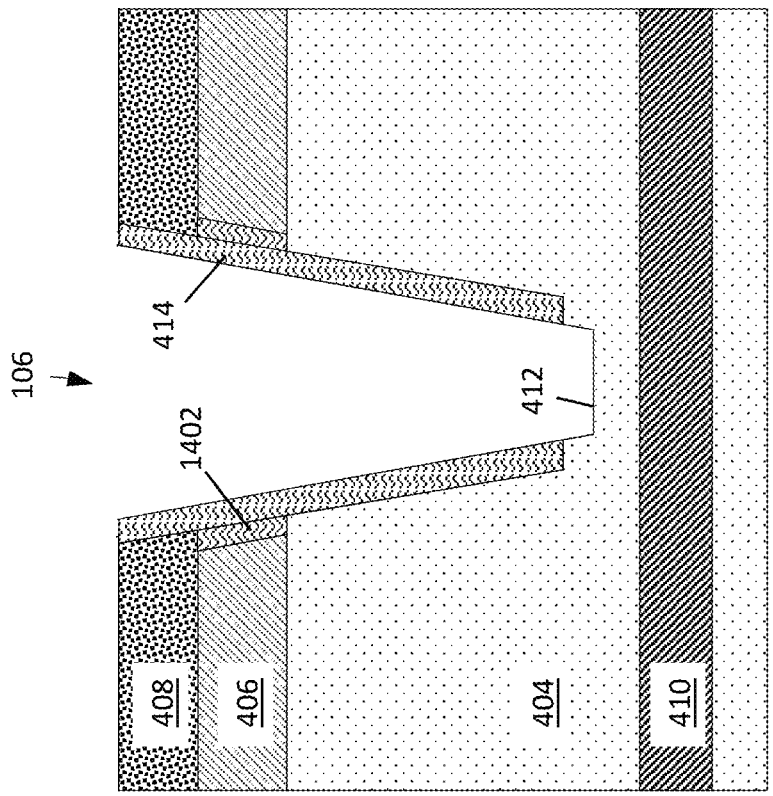

Process 1200 proceeds to act 1212, where the sidewall spacer material is etched to form the resulting sample well, which may involve using similar materials and processes as described in connection with act 508 of process 500. As shown in FIG. 16, an anisotropic etch of spacer layer 1002 removed the horizontal surfaces at the bottom of the sample well and the top surface of the integrated device, such that sidewall spacers 1402 are formed in the resulting sample well 106. In addition, bottom surface 412 of sample well 106 is exposed cladding material (e.g., $SiO_2$). In embodiments where the spacer layer includes $TiO_2$, and results in sidewall spacers having $TiO_2$, a fluorocarbon or $BCl_3$ etch chemistry (with $O_2$ and/or air) may be used. In embodiments where the spacer layer includes $Al_2O_3$, and results in sidewall spacers having $Al_2O_3$, a $BCl_3$ etch chemistry (with $Cl_2$ and/or air) may be used.

Some embodiments involve using a dielectric etch mask, formed over the aperture metal stack, which may protect the top surface of the metal stack during subsequent etching, such as the aperture etch and the sample well etch. The dielectric etch mask may be gradually removed throughout the steps in fabricating the sample well, and in some embodiments may be substantially cleared in the resulting sample well structure. Depending on the type of dielectric material used in the dielectric etch mask, the dielectric etch mask may provide a strong endpoint signal for process control in etching the sample well. The thickness of the top layer depends on the etch selectivity of the dielectric relative to the cladding layer, and the amount of over-etch desired.

Figure 17:
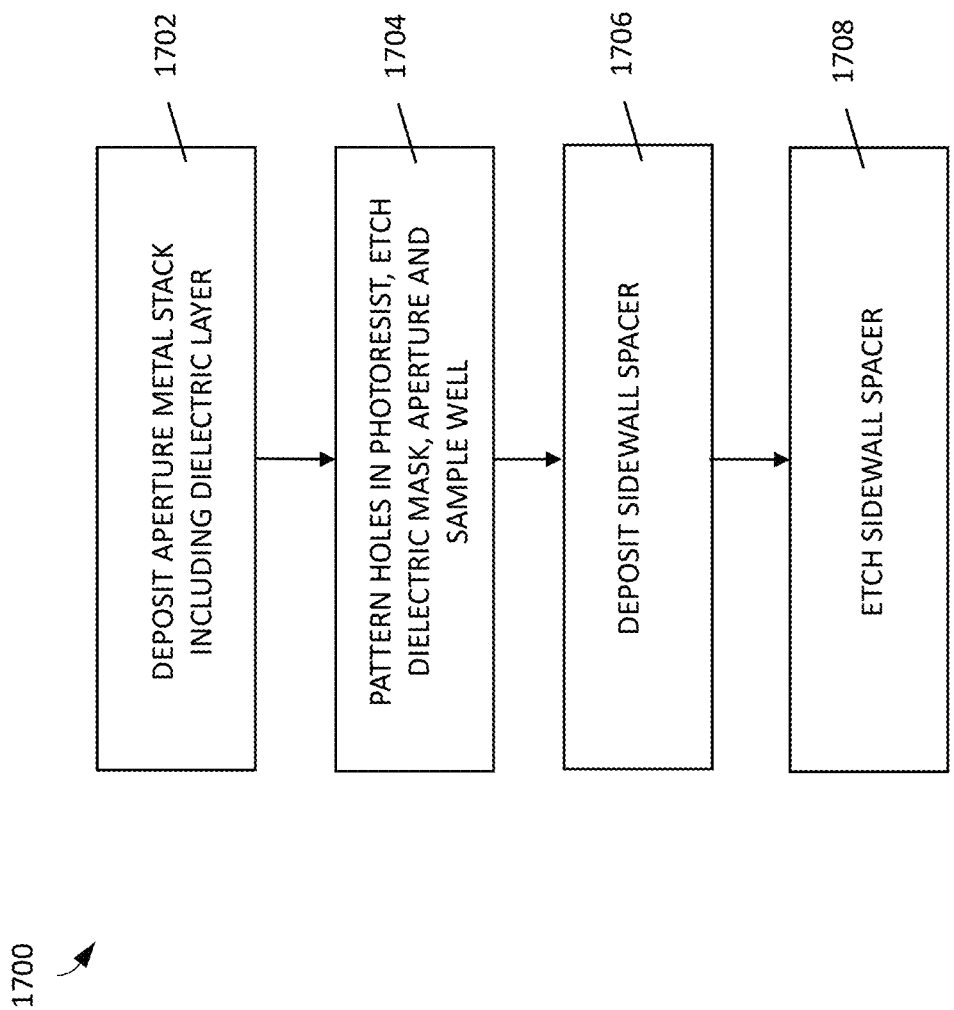
FIG. 17 is a flow diagram illustrating an exemplary process for forming a sample well, in accordance with some embodiments of the technology described herein.
Figure 18:
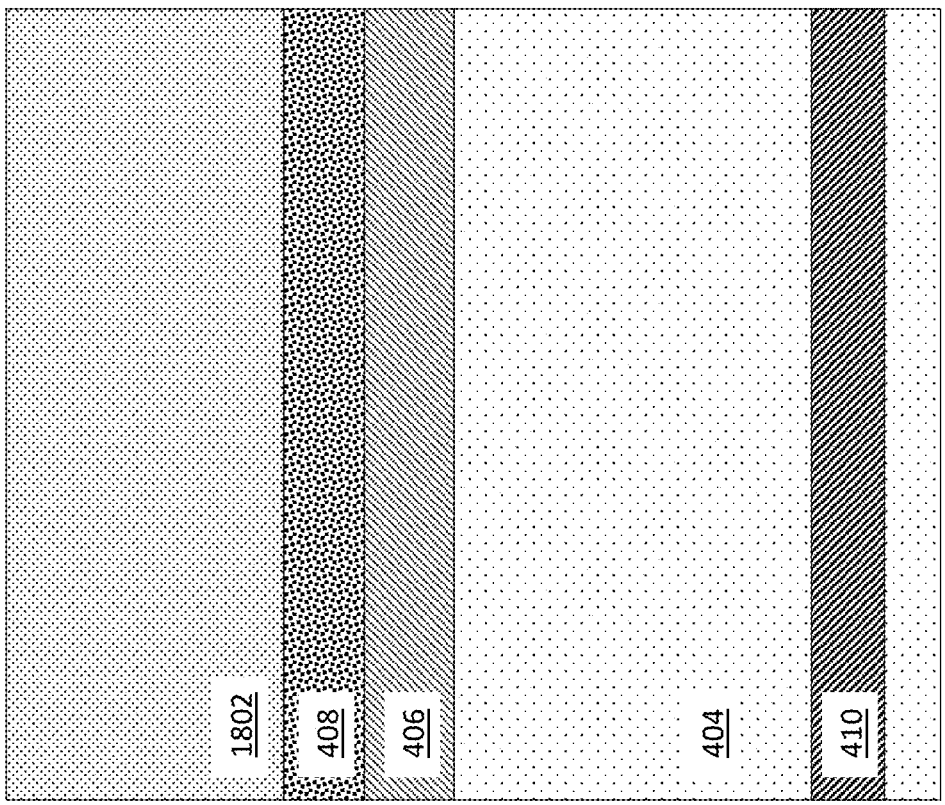

FIG. 17 is a flow diagram illustrating exemplary process 1700 for forming a sample well structure. FIGS. 18-25 show cross-sectional views for some of the steps of process 1700. As shown in FIG. 17, the process 1700 begins at act 1702 by depositing a metal stack over one or more layers, such as a cladding layer or a waveguide. Depositing the metal stack may be performed using processes and materials described above in connection with process 500. In some embodiments, metal stack may include aluminum layer 406 and titanium nitride layer 408 over cladding layer 404 and waveguide 410, as shown in FIG. 18. Act 1702 may further include depositing a dielectric layer over the metal stack. As shown in FIG. 18, dielectric layer 1802 is formed over metal stack, which includes layers 406 and 408. The dielectric layer 1802 may include one or more silicon materials. Examples of suitable materials that may be included in dielectric layer 1802 include amorphous silicon (α-Si), $SiO_2$, SiON, SiN, and silicon alloy (e.g., silicon-rich oxide (SRO) and silicon-rich nitride (SRN)). Dielectric layer 1802 may have a thickness in the range of 30 to 400 nm, or any value or range of values in that range. In some embodiments, dielectric layer 1802 may be PECVD $SiO_2$, deposited at a thickness of about 150-300 nm. In some embodiments, dielectric layer 1802 may be PECVD SiN, deposited at a thickness of about 50-300 nm. In some embodiments, dielectric layer 1802 may be PECVD SiON, deposited at a thickness of about 50-300 nm.

Figure 19:
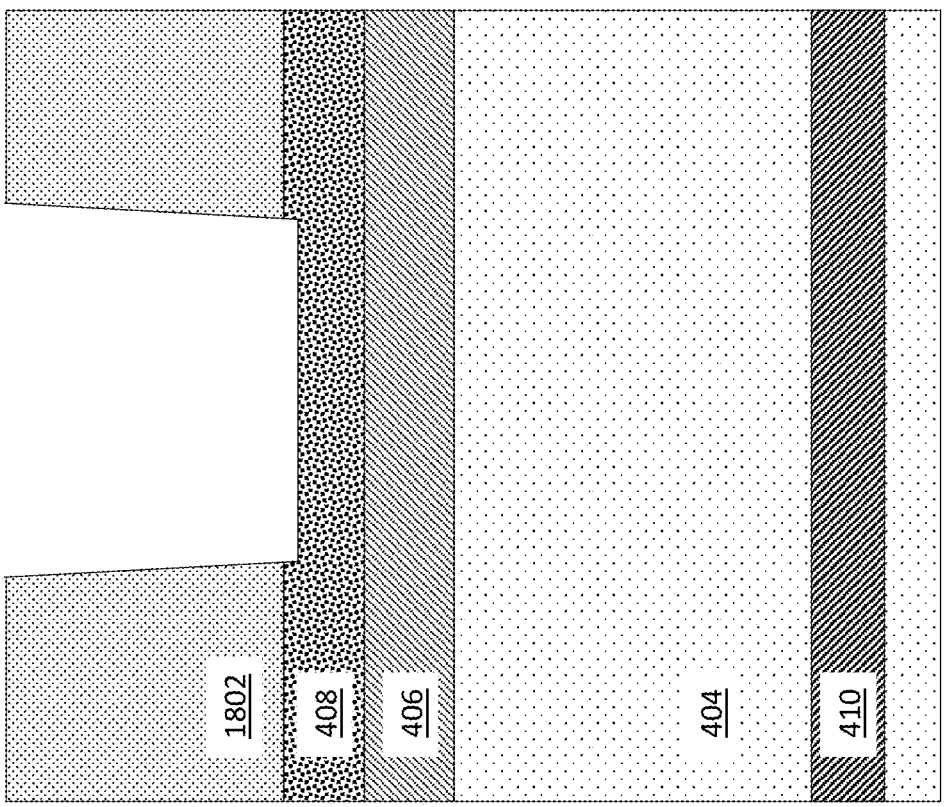
FIGS. 18, 19, 20, 21, 22, 23, 24, and 25 are sequential cross-sectional views illustrating the exemplary process for forming a sample well of FIG. 17.
Figure 20:
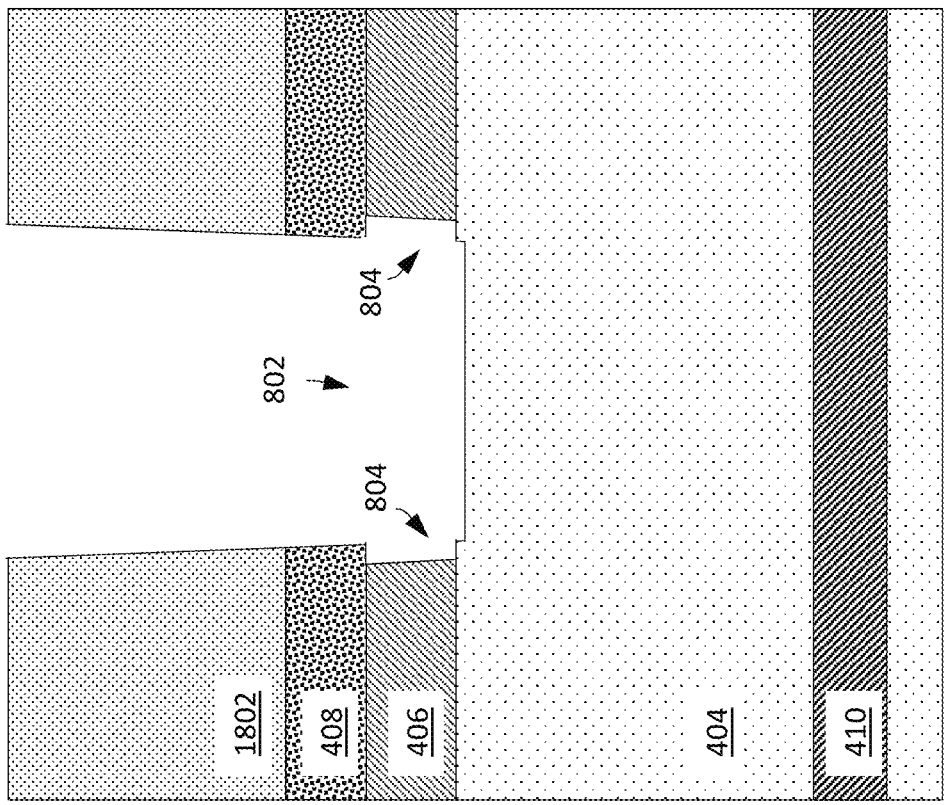

Process 1700 may proceed to act 1704, where a photoresist material is patterned to define aperture openings, and etching an aperture and sample well. The pattern is then etched into the dielectric mask, aperture metal stack, and ultimately the cladding layer to form the sample well. In some embodiments, the photoresist material may be deposited over a BARC layer. In some embodiments, patterned opening may be a circular opening having a diameter in the range of about 150 to 225 nm diameter. Etching the aperture into the metal stack may be performed using processes and materials described above in connection with process 500, and shown in FIG. 7 and FIG. 8. FIG. 19 illustrates a point in the processing following etching of the dielectric layer 1802 and removal of the photoresist material (not shown). With the dielectric layer 1802 patterned as a hardmask, the aperture in metal stack 406, 408 may then be etched as shown in FIG. 20, which shows aperture 802 and undercut regions 804. Etching the aperture into the metal stack may be performed using processes and materials described above in connection with process 500, and shown in FIG. 7 and FIG. 8. In some embodiments, etching of the aperture in the metal stack may involve a plasma etch process, such as a plasma etch process that includes $Cl_2$ and/or $BCl_3$. The plasma metal etching process may be followed by water rinse and/or post-etch cleaning step. At this point, the structure is prepared for the sample well etch into the cladding layer, such as cladding layer 404.

Figure 21:
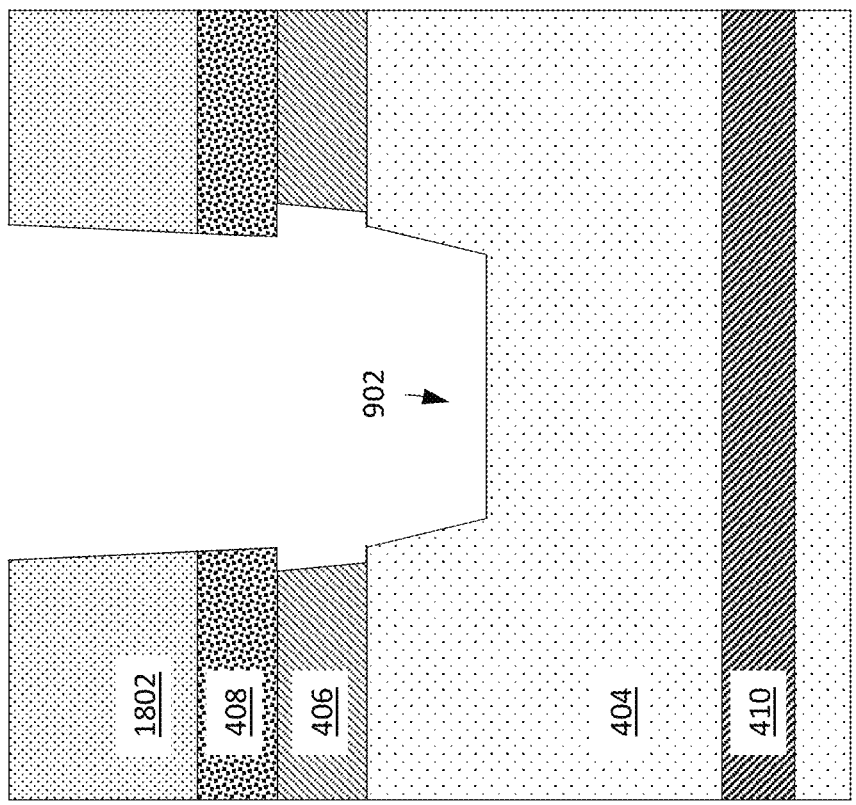
Figure 23:
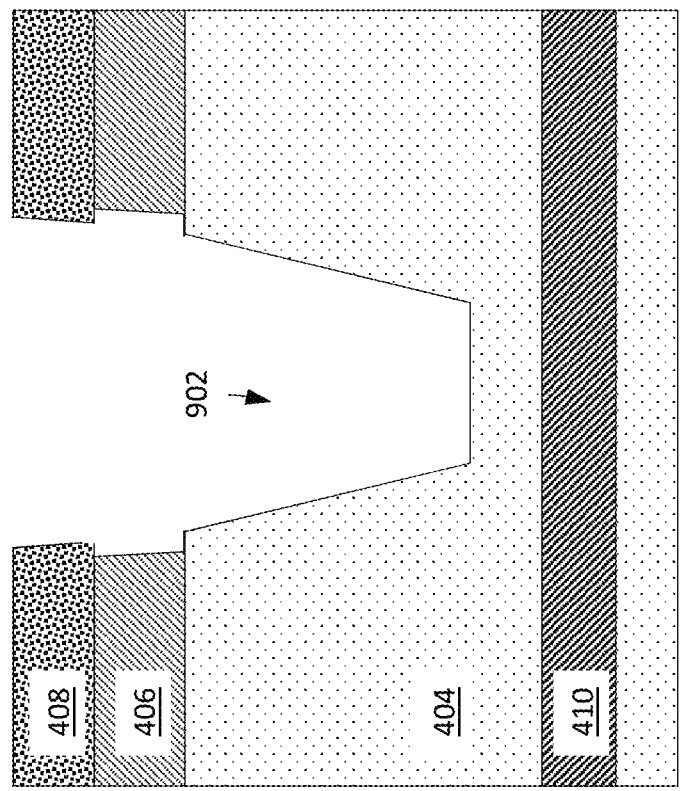
Figure 22:
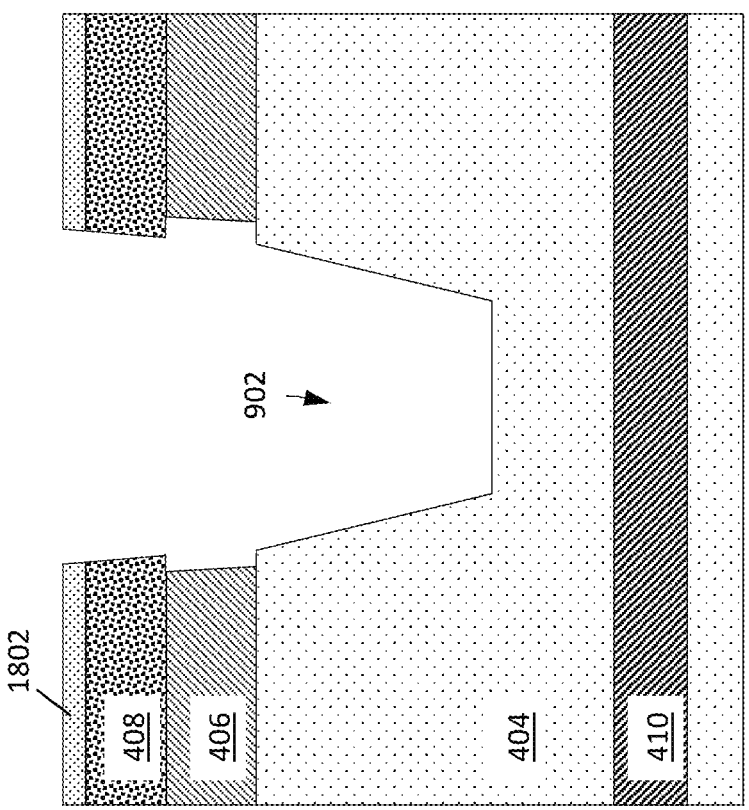

In some embodiments, the dielectric layer 1802 is selected from a material having the same or similar etch characteristics with respect to the cladding layer 404. In such embodiments, the dielectric layer 1802 may be removed as the sample well 902 is etched. An intermediate point in the sample well etch processing is illustrated in FIG. 21, which shows a portion of the dielectric layer 1802 remaining as sample well 902 is at an intermediate stage of being formed. In particular, as compared to FIG. 20, it will be seen from FIG. 21 that the dielectric layer 1802, while still protecting the aperture metal stack 406, 408 from the etching process (e.g., a fluorocarbon based etch), has been reduced in thickness by roughly an amount corresponding to the present etch depth of the sample well 902 being formed. FIG. 22 illustrates a later point in time during the sample well etch process, where the dielectric layer 1802 is mostly consumed and the sample well 902 is mostly etched. Eventually, as shown in FIG. 23, the dielectric layer 1802 is removed as the sample well etch is at or near completion. In particular, the thickness of the dielectric etch mask depend on the etch rate of the dielectric etch mask material during the etch of the sample well, such that the material of the dielectric etch mask is substantially or completely removed at or near the end of the etching of the sample well. In embodiments where the dielectric layer 1802 is $SiO_2$, the dielectric layer 1802 may provide a strong endpoint signal for process control in etching the sample well since the TiN metal layer 408 is exposed once the dielectric etch mask is substantially or completely removed. In such embodiments where $SiO_2$ is used as the dielectric mask material, the thickness of the dielectric layer may correspond to the desired depth of the sample well (e.g., may be slightly less than the desired depth of the sample well) so that the mask is substantially or fully removed when the sample well is etched to the correct depth.

Figure 24:
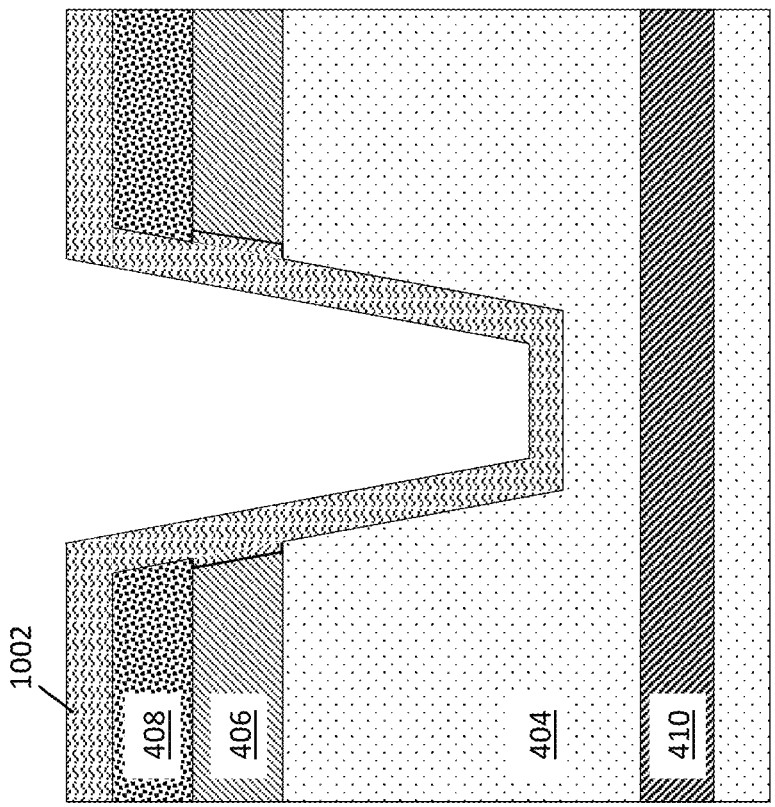

From this point, process 1700 may continue similar to that of process 500. Process 1700 may proceed with act 1706, where a sidewall spacer material is deposited, which may involve using similar materials and processes as described in connection with act 506 of process 500. FIG. 24 shows sidewall spacer material 1002, which contacts both layers 406 and 408. As shown in FIG. 24, undercut regions may form in layer 406 and sidewall spacer material 1002 may fill the undercut regions. Examples of spacer materials that may be used to form sidewall spacer material 1002 include $Al_2O_3$, $TiO_2$, TiN, $Ta_2O_5$, TaN, $ZrO_2$ and $HfO_2$. In some embodiments, the sidewall spacer material 1002 may be a layer of $TiO_2$ formed to a thickness between about 3 nm to about 30 nm. In some embodiments, the sidewall spacer material 1002 may be a layer of $TiO_2$ formed to a thickness of about 12 nm by atomic layer deposition (ALD) at a temperature of about 230° C.

Figure 25:
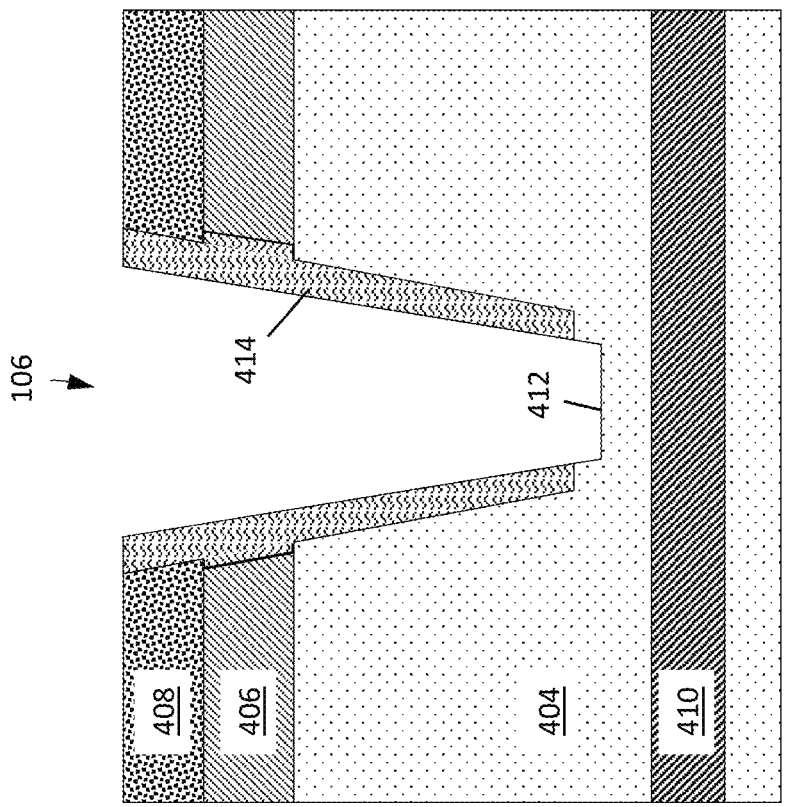

Process 1700 proceeds to act 1708, where the sidewall spacer material is etched to form the resulting sample well, which may involve using similar materials and processes as described in connection with act 508 of process 500. As shown in FIG. 25, an anisotropic etch of spacer layer 1002 removed the horizontal surfaces at the bottom of the sample well and the top surface of the integrated device, such that sidewall spacers 414 are formed in the resulting sample well 106. In addition, bottom surface 412 of sample well 106 is exposed cladding material (e.g., $SiO_2$). In embodiments where the spacer layer includes $TiO_2$, and results in sidewall spacers having $TiO_2$, a fluorocarbon or $BCl_3$ etch chemistry (with $O_2$ and/or air) may be used. In embodiments where the spacer layer includes $Al_2O_3$, and results in sidewall spacers having $Al_2O_3$, a $BCl_3$ etch chemistry (with $Cl_2$ and/or air) may be used.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

The described embodiments can be implemented in various combinations. Example configurations include methods (1)-(33), and integrated devices (34)-(43) below.

(1) A method of forming an integrated device, the method comprising: forming a metal stack over a cladding layer; forming an aperture in the metal stack; forming first spacer material within the aperture; and forming a sample well by removing some of the cladding layer to extend a depth of the aperture into the cladding layer, wherein at least one portion of the first spacer material is in contact with at least one layer of the metal stack.

(2) The method of (1), wherein forming the metal stack further comprises forming the metal stack on the cladding layer.

(3) The method of (1) or (2), wherein forming the first spacer material further comprises forming the first spacer material over the metal stack and at a bottom surface of the aperture.

(4) The method of any one of (1)-(3), wherein forming the sample well further comprises performing a first directional etch to remove at least some of the first spacer material disposed on a top surface of the metal stack and on a bottom surface of the aperture.

(5) The method of any one of (1)-(4), wherein the first spacer material includes at least one material configured to reduce formation of metal fluoride residue during an etch process used in forming the sample well.

(6) The method of any one of (1)-(5), wherein the first spacer material includes at least one material configured to reduce formation of metal fluoride residue on at least one metal layer of the metal stack during an etch process used in forming the sample well.

(7) The method of any one of (1)-(6), wherein the at least one portion of the first spacer material is disposed at an undercut region of the metal stack.

(8) The method of any one of (1)-(7), wherein the metal stack comprises at least one aluminum containing layer and at least one titanium containing layer.

(9) The method of any one of (1)-(8), wherein the first spacer material is formed by plasma enhanced chemical vapor deposition (PECVD).

(10) The method of any one of (1)-(9), wherein the first spacer material includes at least one silicon material.

(11) The method of any one of (1)-(10), wherein the first spacer material comprises one or more layers selected from the group of: amorphous silicon ($\alpha$-Si), $SiO_2$, SiON, SiN, and silicon alloy.

(12) The method of any one of (1)-(11), wherein the first spacer material is formed by atomic layer deposition (ALD).

(13) The method of any one of (1)-(12), wherein the first spacer material comprises one or more layers selected from the group of: $TiO_2$, $Al_2O_3$, $SiO_2$, $HfO_2$, TiN, $Ta_2O_5$, and $ZrO_2$.

(14) The method of any one of (1)-(13), wherein the cladding layer comprises $SiO_2$.

(15) The method of any one of (1)-(14), further comprising: forming second spacer material into the sample well; and removing at least some of the second spacer material at a bottom surface of the sample well to expose a portion of the cladding layer, wherein at least one portion of the second spacer material is in contact with one or more of the metal stack, the at least one portion of the first spacer material, and the cladding later.

(16) The method of (15), wherein forming the second spacer material further comprises forming the second spacer material over the metal stack.

(17) The method of (15) or (16), wherein removing the at least some of the second spacer material further comprises performing a directional etch to remove second spacer material disposed on a top surface of the metal stack and on the bottom surface of the sample well.

(18) The method of (17), wherein the directional etch comprises a fluorocarbon based etch.

(19) The method of any one of (15)-(18), wherein the second spacer material is formed by atomic layer deposition (ALD).

(20) The method of any one of (15)-(19), wherein the second spacer material comprises one or more layers selected from the group of: $TiO_2$, $Al_2O_3$, $HfO_2$, $ZrO_2$, and $Ta_2O_5$.

(21) A method of forming an integrated device, the method comprising: forming a metal stack over a cladding layer; forming a dielectric layer over the metal stack; forming an aperture in the metal stack by forming an opening in the dielectric layer and using the dielectric layer as a mask in removing a portion of the metal stack; and forming a sample well by removing a portion of the cladding layer, wherein at least a portion of dielectric layer is removed while forming the sample well.

(22) The method of (21), wherein forming the metal stack further comprises forming the metal stack on the cladding layer.

(23) The method of (21) or (22), wherein forming the dielectric material further comprises forming the dielectric layer on the metal stack.

(24) The method of any one of (21)-(23), wherein forming the aperture further comprises etching the opening in the dielectric layer and using the dielectric layer as an etch mask to form the aperture in the metal stack.

(25) The method of any one of (21)-(24), wherein forming the sample well further comprises etching the cladding layer and the dielectric layer simultaneously.

(26) The method of any one of (21)-(25), wherein the metal stack comprises at least one aluminum containing layer and at least one titanium containing layer.

(27) The method of any one of (21)-(26), wherein the cladding layer comprises $SiO_2$.

(28) The method of any one of (21)-(27), further comprising: forming a spacer layer over the metal stack and into the sample well; and performing a directional etch to remove portions of the spacer layer disposed on a top surface of the metal stack and on a bottom surface of the sample well to expose a portion of the cladding layer; wherein at least one portion of the spacer layer forms at least one sidewall of the sample well.

(29) The method of (28), wherein the spacer layer is formed by atomic layer deposition (ALD).

(30) The method of (28) or (29), wherein the spacer layer comprises one or more layers selected from the group of: $TiO_2$, $Al_2O_3$, $HfO_2$, $ZrO_2$, and $Ta_2O_5$.

(31) The method of any one of (21)-(30), wherein forming the sample well further comprises substantially removing the dielectric layer.

(32) The method of any one of (21)-(31), wherein the integrated device after forming the sample well does not include the dielectric layer.

(33) The method of any one of (21)-(32), wherein the dielectric layer comprises one or more selected from the group of: amorphous silicon ($\alpha$-Si), $SiO_2$, SiON, SiN, and silicon alloy.

(34) An integrated device comprising: a cladding layer; a metal stack formed over the cladding layer and having at least one undercut region; a sample well extending through the metal stack proximate to the at least one undercut region and into the cladding layer; and a first spacer material filling the at least one undercut region.

(35) The integrated device of configuration (34), wherein the first spacer material forms at least one sidewall of the sample well.

(36) The integrated device of configuration (34) or (35), wherein the first spacer material comprises one or more selected from the group of: amorphous silicon ($\alpha$-Si), $SiO_2$, SiON, and SiN.

(37) The integrated device of any one of configurations (34)-(36), wherein the first spacer material comprises one or more selected from the group of: $TiO_2$, $Al_2O_3$, $HfO_2$, TiN, $ZrO_2$, and $Ta_2O_5$.

(38) The integrated device of any one of configurations (34)-(37), wherein the metal stack comprises at least one layer including aluminum and at least one layer including titanium.

(39) The integrated device of any one of configurations (34)-(38), wherein the cladding layer comprises $SiO_2$.

(40) The integrated device of any one of configurations (34)-(39), further comprising a second spacer material in contact with one or more of the metal stack, the first spacer material, and the cladding layer.

(41) The integrated device of configuration (40), wherein the second spacer material forms at least one sidewall of the sample well.

(42) The integrated device of configuration (40) or (41), wherein the second spacer material comprises one or more layers selected from the group of: $TiO_2$, $Al_2O_3$, $HfO_2$, $ZrO_2$, and $Ta_2O_5$.

(43) The integrated device of any one of configurations (34)-(42), wherein the metal stack comprises a first layer formed over a second layer, and the undercut region is formed in the second layer.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An integrated device comprising:
   a cladding layer;
   a metal stack formed over the cladding layer and having at least one undercut region;
   a sample well extending through the metal stack proximate to the at least one undercut region and into the cladding layer; and a first spacer material filling the at least one undercut region.

2. The integrated device of claim 1, wherein the first spacer material forms at least one sidewall of the sample well.

3. The integrated device of claim 1, wherein the first spacer material comprises one or more selected from the group of: amorphous silicon (α-Si), $SiO_2$, SiON, and SiN.

4. The integrated device of claim 1, wherein the first spacer material comprises one or more selected from the group of: $TiO_2$, $Al_2O_3$, $HfO_2$, TiN, $ZrO_2$, and $Ta_2O_5$.

5. The integrated device of claim 1, wherein the metal stack comprises at least one layer including aluminum and at least one layer including titanium.

6. The integrated device of claim 1, wherein the cladding layer comprises $SiO_2$.

7. The integrated device of claim 1, further comprising a second spacer material in contact with one or more of the metal stack, the first spacer material, and the cladding layer.

8. The integrated device of claim 7, wherein the second spacer material forms at least one sidewall of the sample well.

9. The integrated device of claim 7, wherein the second spacer material comprises one or more layers selected from the group of: $TiO_2$, $Al_2O_3$, $HfO_2$, $ZrO_2$, and $Ta_2O_5$.

10. The integrated device of claim 1, wherein the metal stack comprises a first layer formed over a second layer, and the undercut region is formed in the second layer.

\* \* \* \* \*